United States Patent
Henke (12)

(10) Patent No.: US 6,399,653 B1
(45) Date of Patent: Jun. 4, 2002

(54) RING FUSED DIHYDROPYRANS, PROCESS FOR PREPARATION AND USE THEREOF

(75) Inventor: Stephan Henke, Hofheim (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/609,594

(22) Filed: Jun. 30, 2000

Related U.S. Application Data

(63) Continuation of application No. 09/202,558, filed as application No. PCT/EP97/03146 on Jun. 18, 1997, now abandoned.

(30) Foreign Application Priority Data

Jun. 18, 1996 (DE) .......................... 196 24 154

(51) Int. Cl.⁷ ...................... A61K 31/35; C07D 493/00; C07D 323/04
(52) U.S. Cl. ........................ 514/454; 514/455; 514/456; 514/459; 514/460; 549/361; 549/364; 549/386; 549/387; 549/398; 549/399
(58) Field of Search ................................. 549/361, 364, 549/386, 387, 398, 399; 514/454, 455, 456, 459, 460

(56) References Cited

U.S. PATENT DOCUMENTS 3,775,435 A 11/1973 Sellstedt et al. ............ 549/402

5,767,116 A 6/1998 Kerrigan et al. ....... 514/217.03

OTHER PUBLICATIONS

Garrat, Vollhardt, Aromatizität, "7. Heterocyclische Systeme" pp. 131–153 (1973) Stuttgart.

Früchtel et al., "Organic Chemistry on Solid Supports", Agnew. Chem. Int. Ed. Engl. 35:17–42 (1996).

L.F. Tietze, "Domino–Reactions: The Tandem–Knoevenagel–Hetero–Diels–Alder Reaction And Its Application In Natural Product Synthesis", J. Heterocyclic Chem., 27(47):47–71 (1990).

Primary Examiner—Amelia Owens
(74) Attorney, Agent, or Firm—Finnegan, Henderson, Farabow, Garrett & Dunner, L.L.P.

(57) ABSTRACT

The invention relates to compounds of the formula I

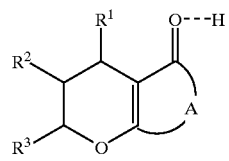

in which the radicals $R^1$, $R^2$, $R^3$ and A have the meaning mentioned in the description. The invention further relates to a process for the preparation of the compounds of the formula I by means of solid-phase synthesis, and use thereof as pharmaceuticals.

18 Claims, No Drawings

RING FUSED DIHYDROPYRANS, PROCESS FOR PREPARATION AND USE THEREOF

This is a continuation of application Ser. No. 09/202,558 filed on Dec. 17 1998, now abandoned which is a 371 national stage filing of PCT/EP97/03146, filed Jun. 18, 1997, all of which are incorporated herein by reference.

The invention relates to compounds of the formula I

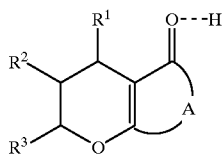

in which:
$R^1$ is
1. $(C_1–C_{14})$-alkyl,
2. $(C_2–C_6)$-alkenyl,
3. $(C_0–C_6)$-alkyl-$(C_3–C_{10})$-cycloalkyl-$(C_0–C_6)$-alkyl, where the alkyl moiety is optionally substituted by one or more OH groups,
4. $(C_0–C_6)$-alkyl-$(C_6–C_{14})$-aryl,
5. $(C_0–C_6)$-alkyl-$(C_3–C_9)$-heteroaryl,
6. $(C_2–C_6)$-alkenyl-$(C_6–C_{14})$-aryl,
7. $(C_2–C_6)$-alkenyl-$(C_3–C_9)$-heteroaryl,
8. $(C_1–C_6)$-alkanoyl,
9. a radical as defined under 4., 5., 6. or 7., where the $(C_6–C_{14})$-aryl or $(C_3–C_9)$-heteroaryl moiety is substituted by 1, 2 or 3 identical or different radicals from the group consisting of $(C_1–C_{10})$-alkyl, carboxyl, amino, nitro, $(C_1–C_4)$-alkylamino, hydroxyl, $(C_1–C_4)$-alkoxy, where one to all hydrogen atoms can be replaced by fluorine atoms, $(C_6–C_{12})$-aryloxy, halogen, cyano, di-$(C_1–C_4)$-alkylamino, carbamoyl, sulfamoyl and $(C_1–C_4)$-alkoxycarbonyl, or two adjacent radicals on the $(C_6–C_{12})$-aryl ring together are alkylenedioxy, preferably methylenedioxy;

$R^2$ is hydrogen, $(C_1–C_{10})$-alkyl, $(C_0–C_6)$-alkyl-$(C_6–C_{12})$-aryl or $(C_0–C_6)$-alkyl-$(C_3–C_9)$-heteroaryl, where the $C_6–C_{12}$-aryl or $C_3–C_9$-heteroaryl moiety is optionally substituted by 1, 2 or 3 identical or different radicals from the group consisting of carboxyl, amino, $(C_1–C_4)$-alkylamino, hydroxyl, $(C_1–C_4)$-alkoxy, halogen, cyano, di-$(C_1–C_4)$-alkylamino, carbamoyl, sulfamoyl and $(C_1–C_4)$-alkoxycarbonyl;

$R^3$ is —X—$R^4$;
X is —O—, —$NR^5$— or —S—;
$R^4$ is defined as $R^1$;
where $R^4$ together with $R^2$ can form a bridge member —$CH_2$—$CH_2$— or —$CH_2$—$CH_2$—$CH_2$—;
$R^5$ is hydrogen or $(C_1–C_6)$-alkyl;
A is a fused cyclic ring system which
a) is substituted by one, two or three, preferably by one or two, oxo or hydroxyl functions, where one hydroxyl or oxo function is in the neighboring position to the dihydropyran ring, and
b) is mono, di- or polysubstituted, preferably mono- or disubstituted, by a $(C_1–C_{10})$-alkyl radical or a carboxyl group, where at least one alkyl substituent carries a functional group, such as hydroxyl, carboxyl or amino;
and physiologically tolerable salts thereof.

Examples of fused cyclic ring systems A are 5- or 6-membered ring structures which can be aromatic or non-aromatic and can carry oxygen or nitrogen in the ring structure. Cyclopentane, cyclohexane, tetrahydrofuran, benzene, pyridine, imidazole, pyrazole, piperazine, dioxane and pyrimidine are particularly suitable.

$(C_6–C_{14})$-Aryl is understood as meaning, for example, phenyl, naphthyl, anthracenyl or biphenyl.

Alkyl and radicals derived therefrom such as alkoxy can be straight-chain or branched. Halogen is preferably fluorine, chlorine or bromine.

A heteroaryl radical in the sense of the present invention is the radical of a monocyclic or bicyclic $(C_3–C_9)$-heteroaromatic, which contains one or two N atoms and/or an S or an O atom in the ring system. For the term "heteroaromatic" see Garrat, Vollhardt, Aromatizität [Aromaticity], Stuttgart 1973, pages 131–153. Examples of suitable heteroaryl radicals are the radicals of thiophene, furan, benzo[b]thiophene, benzofuran, pyrrole, imidazole, pyrazole, pyridine, pyrazine, pyrimidine, pyridazine, indole, quinoline, isoquinoline, oxazole, isoxazole, thiazole, isothiazole, isobenzofuran, indolizine, isoindole, indazole, phthalazine, naphthyridine, quinoxaline, quinazoline, cinnoline and furazane.

Aryl, alkyl, heteroaryl and radicals derived therefrom can be mono- substituted or, if chemically possible, also polysubstituted as indicated above.

Functional groups such as hydroxyl, carboxyl or amino can also be provided with a customary chemical protective group.

Chiral centers, if not stated otherwise, can be present in the R or in the S configuration. The invention relates both to the optically pure compounds and to stereoisomer mixtures such as enantiomer mixtures and diastereomer mixtures.

The hydroxyl or oxo groups situated on the fused ring system A can be present in all tautomeric forms.

Possible salts are, in particular, alkali metal and alkaline earth metal salts, salts with physiologically tolerable amines and salts with inorganic or organic acids such as, for example, HCl, HBr, $H_2SO_4$, maleic acid or fumaric acid.

The compounds of the formula I described above are derivatives of dihydropyran, which can be synthesized rapidly, in an automated manner and in good yields on a solid support material (solid-phase synthesis) with the aid of combinatorial methods.

The compounds described above have a pharmacological action on various forms of disorder, such as metabolic disorders, e.g. diabetes and arteriosclerosis, on disorders of the cardiovascular system and of the central nervous system and on disorders of bone metabolism. They have immunomodulating properties and are suitable for the treatment of cancer and autoimmune disorders. An antiinfective action can moreover be observed.

Preferred compounds of the formula I are those in which $R^1$ is $(C_1–C_8)$-alkyl, $(C_0–C_6)$-alkyl-$(C_6–C_{12})$-aryl, $(C_0–C_6)$-alkyl-$(C_3–C_9)$-heteroaryl or $(C_0–C_6)$-alkyl-$(C_6–C_{12})$-aryl, where the $(C_6–C_{12})$-aryl moiety is substituted by 1, 2 or 3 identical or different radicals from the group consisting of $(C_1-C_6)$-alkyl, carboxyl, amino, nitro, hydroxyl, $(C_1-C_6)$-alkoxy, halogen or two adjacent radicals on the $(C_6-C_{12})$-aryl ring are together methylenedioxy;

$R^2$ is hydrogen or $(C_1-C_6)$-alkyl, preferably hydrogen;

$R^3$ is —X—$R^4$;

X is —O—, NR or —S—;

$R^4$ is $(C_1-C_6)$-alkyl which is optionally substituted by one or two radicals from the group consisting of OH, $NR^5$; $(C_0-C_6)$-alkyl-$(C_6-C_{12})$-aryl, preferably phenyl or benzyl; $(C_3-C_6)$-cycloalkyl or $(C_1-C_6)$-alkanoyl and where $R^4$ together with $R^2$ can form a bridge member —$CH_2$—$CH_2$— or —$CH_2$—$CH_2$—$CH_2$—;

$R^5$ is hydrogen or $(C_1-C_6)$-alkyl; and physiologically tolerable salts thereof.

Compounds of the formula I are further preferred in which $R^1$ is $(C_1-C_6)$-alkyl or $(C_0-C_6)$-alkyl-$(C_6-C_{12})$-aryl, for example phenyl or benzyl. Compounds of the formula I are also preferred in which $R^2$ is hydrogen or $(C_1-C_6)$-alkyl, and also compounds of the formula I in which X is —O—.

Compounds of the formula I are further preferred in which the fused cyclic ring system A is 1,3-pyrimidine, benzene, dioxane or cyclohexane.

The synthesis is generally carried out by means of a suitable binding of cyclic 1,3-dicarbonyl compounds via a chemical linker to a polymeric matrix according to methods known to the person skilled in the art. Suitable polymeric matrices are, for example, polystyrene, polytetrafluoroethylene, polyacrylamide, which can optionally be extended with polyethylene chains (spacers) to improve the swellability. Suitable linker units are structures which specifically release the synthesized compound by means of acid, base, reduction, oxidation, by light or with fluoride ions, the linker unit remaining on the polymeric matrix (for a general survey of linker groups in solid-phase synthesis see J. Früchtel, G. Jung, Angew. Chemie Int. Ed. 1996, 35, 17–42).

The 1,3-dicarbonyl compounds linked to the polymer in such a way via a suitable functional group, such as —COOH, —OH, —$NH_2$, can be subjected to further customary reactions of organic chemistry. Synthesis on the solid phase in this case has the advantage that reagents and reactants can be used in a large excess, solvents can be widely varied and purification is effected by simple washing of the resin particles. After carrying out the synthesis stages sequentially, removal of the newly synthesized compounds is effected with the aid of specific reagents, according to the choice of linker (for a description of solid-phase synthesis see: J. Früchtel, G. Jung Angew. Chemie Int. Ed. 1996, 35, 17–42).

The solid-phase synthesis of ring-fused dihydropyran structures can be carried out by means of a tandem Knoevenagel-Diels-Alder reaction (L. F. Tietze et al, J. Heterocyclic Chemistry 1990, 27, 47f) (Scheme 1; Li=linker, P=polymeric matrix).

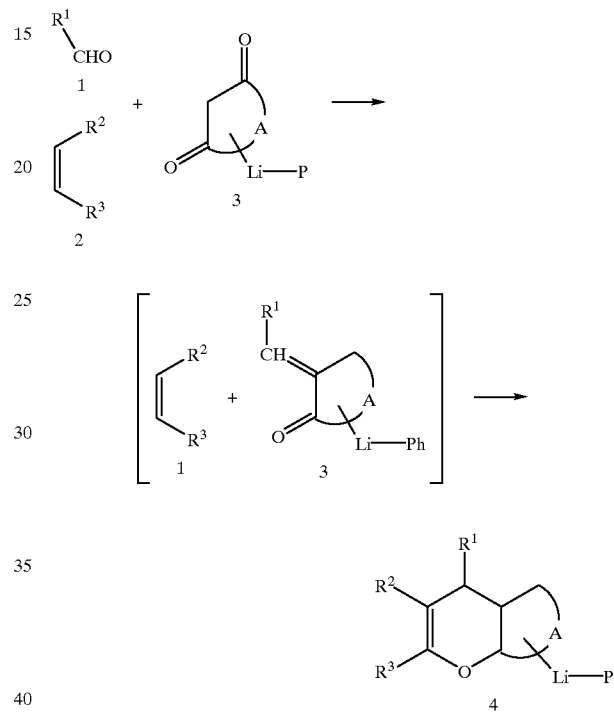

Scheme 1

Preparation Process

A. Synthesis of polymer-bound 1,3-dioxocyclohexane-5-carboxylic acid

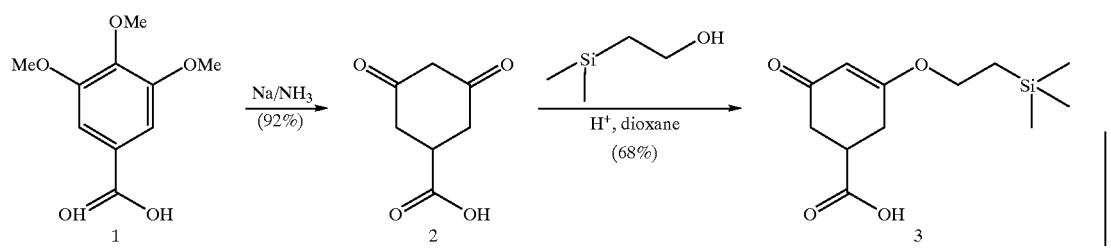

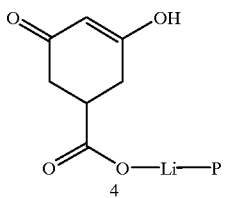  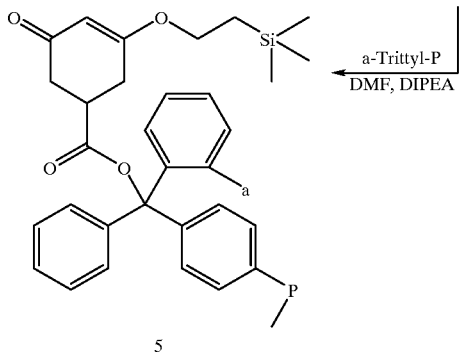

capacity: 0.5 mmol/g

1. Synthesis of (3)

60 g of the diketone (2) known from the literature are dissolved in 300 ml of dioxane abs. and 1 ml of conc. sulfuric acid is added. 54 ml of 2-trimethylsilylethanol are added and the mixture is allowed to react at room temperature for 24 h. After chromatography on silica gel, 38 g of (3) are obtained.

2. Synthesis of (5)

50 g of commercial 2-chlorotritylpolystyrene resin (Novabiochem), which is crosslinked with 2% divinylbenzene, are suspended in 300 ml of DMF and swollen over the course of 10 min. 11.0 g of (3) and 14.4 ml of N-ethylmorpholine are added. After 18 h at room temperature, the solution is separated off from the resin through a frit and the resin is washed thoroughly with DMF and methylene chloride. The resin is incubated with methanol over the course of 10 min and again washed thoroughly with DMF and methylene chloride. 60 g of (5) are obtained.

3. Synthesis of (4)

50 g of (5) are treated with 16.5 g of tetrabutylammonium fluoride (TBAF) and 300 ml of DMF abs. and shaken at room temperature for 4 h. The solution is filtered off with suction through a frit and the resin is washed thoroughly with DMF and methylene chloride. After drying in vacuo, 57 g of (4) are obtained. Removal of a sample with acetic acid yields (2) in 95% purity (HPLC, MS). The resin loading is determined as 0.5 mmol/g.

B. Synthesis of the cyclohexane- and benzene-fused dihydropyrans (scheme 2)

here, by way of example: $R^1$=n-hexyl, $R^2$=H, $R^3$=—O-tert-butyl

Scheme 2

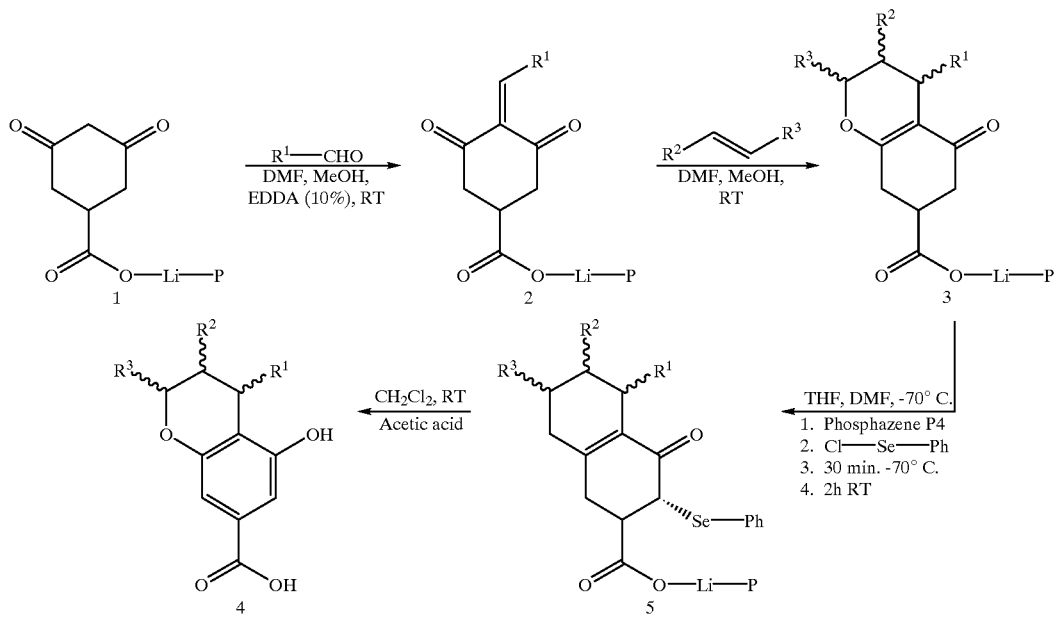

1. Synthesis of (3)

300 mg of (1) are preswollen in 0.2 ml of methylene chloride and treated with 60 μl of 1-heptanal and 2 ml of methanol. 10 mg of ethylene-diammonium diacetate are added and the mixture is allowed to react at room temperature for 2 h. 0.5 ml of tert-butyl vinyl ether is then added and the suspension is shaken at room temperature for a further 64 h. After removal of the solution through a frit, the resin is washed thoroughly with methylene chloride. After drying, about 330 mg of (3) remain. After removal of the polymer by treatment with acetic acidmethylene chloride and evaporation of the solvent, 3.4 mg of the free dihydropyran (3, Li-P=H) are obtained as a diastereomer mixture (HPLC/MS).

2. Synthesis of (4)

1 g of (3) is cooled to −70° C. in 6 ml of DMF abs. and 4 ml of THF abs. under argon. After addition of 2.5 ml of phosphazene P$_4$, the mixture is allowed to react at −70° C. of or 3 h. A solution of 191 mg of phenylselenyl chloride in 2 ml of THF abs. is then added, and the mixture is then allowed to react for 30 min at −70° C. and for 2 h at room temperature. It is then filtered off with suction using DMF and washed with buffer, pH 6, CH$_3$OH and MTB+toluene. The resin is removed overnight using 9:1 CH$_2$Cl$_2$/acetic acid at room temperature. 118 mg of (4) are obtained.

C. Synthesis of 1,3-dioxane-fused dihydropyrans (Scheme 3)

here by way of example with R$^1$=hexyl

Scheme 3

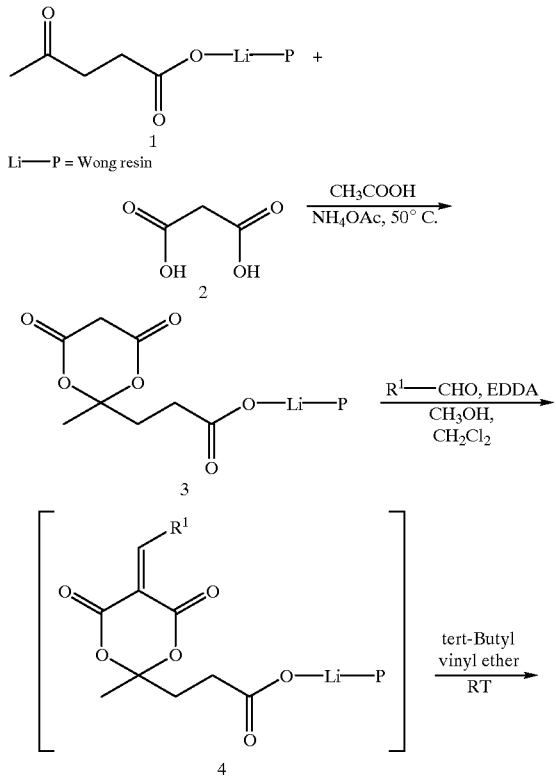

-continued

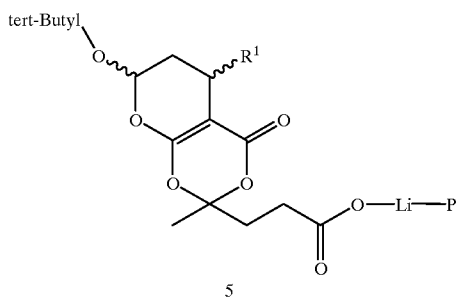

1. Synthesis of the resin-bound Meldrum's acid derivative (3)

50 g of resin-bound 2-oxopentanecarboxylic acid (1) are swollen in 200 ml of acetic acid and treated with 20 g of malonic acid (2). 10 g of anhydrous ammonium acetate are added and the mixture is heated to 50° C. After stirring carefully for 3 h, the resin is freed from the solution, washed thoroughly with DMF and methylene chloride and dried. 53 g of (3) are obtained. Removal of a sample using anhydrous TFA yields the free Meldrum's. acid derivative (3, Li-P=H) (HPLC, MS).

2. Synthesis of (5)

1 g of (3), EDDA, 3 ml of CH$_2$Cl$_2$, 20 ml of CH$_3$OH abs. and 300 μl of n-heptanal are allowed to react at room temperature for 2 min. After addition of 3 ml of tert-butyl vinyl ether, the mixture is allowed to react at room temperature for 24 h. The resin is filtered off with suction and washed with DMF and MTB ether (5). The resin is removed at room temperature in 9:1 CH$_2$Cl$_2$/acetic acid over the course of 24 h, the mixture is filtered and the filtrate is evaporated.

D. 1,3-Pyrimidin-2-one-fused dihydropyrans can be synthesized, for example, according to the following scheme Scheme 4

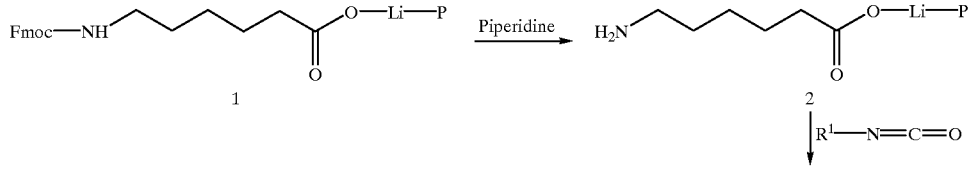

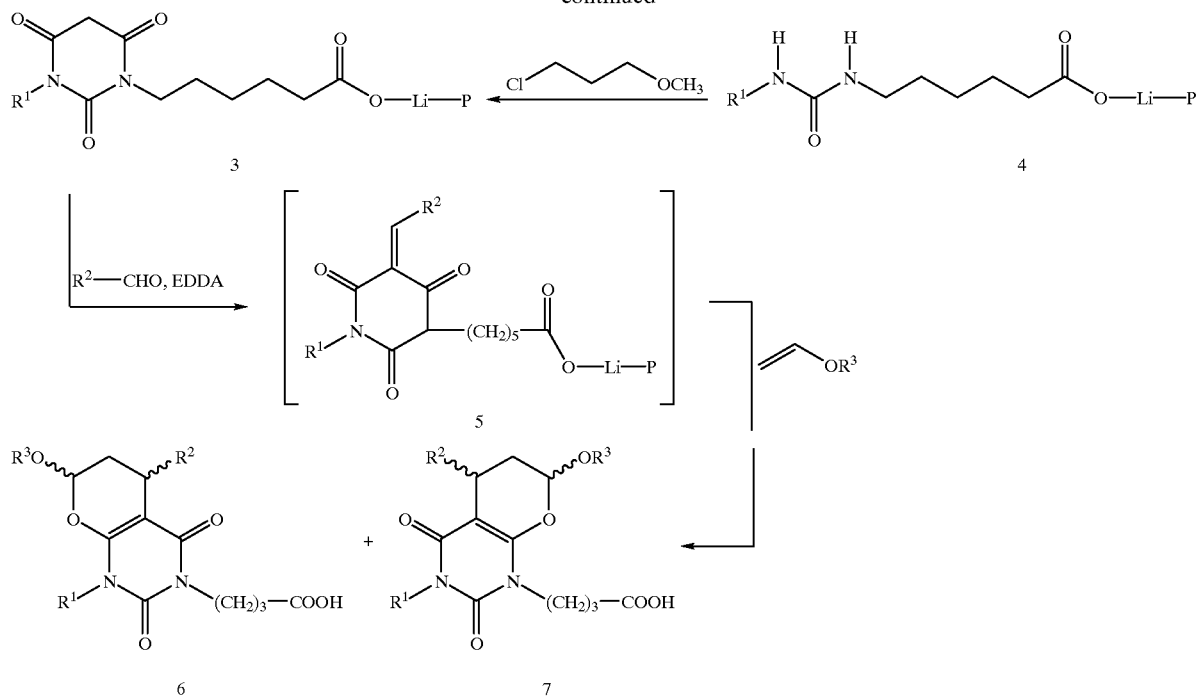

1. Synthesis of (4)

About 200 mg of polymer-bound protected aminohexanecarboxylic acid (Novabiochem) are swollen in solvent (e.g. DMF) and treated with about 0.5 ml of piperidine. The mixture is stirred at room temperature for about 30 min, and the resin is freed from the solution and washed thoroughly with solvent (e.g. DMF). It is taken up again in solvent (e.g. 2 ml of DMF) and about 1 mmol of the isocyanate and about 0.3 ml of triethylamine are added. The mixture is stirred at room temperature for about 8 h. The resin is then freed from the solution and washed thoroughly with solvent (e.g. DMF and methylene chloride). After drying, (4) is obtained. The free urea derivative (4, Li-P=H) is obtained by removal of the linker.

2. Synthesis of (3)

About 200 mg of (4) are swollen in solvent in the cold (e.g. at 0° C. in DMF) and treated with about 1 mmol of monomethyl chloromalonate. About 0.5 ml of triethylamine is added and the mixture is stirred for about 2 h at 0° C. and for 1 h at a low heat (e.g. 50° C.). After washing the resin (3) is isolated. The free derivative of the N,N'-dialkylbarbituric acid (3, Li-P=H) is then obtained by removal of the linker.

3. Synthesis of (6) and (7)

About 300 mg of (3) are treated with about 0.5 mmol of the aldehyde and swollen in DMF. About 10 mg of ethylenediammonium diacetate and about 1 ml of methanol and also 1 ml of the enol ether are added and the mixture is stirred for about 8 h at low heat (e.g. 40° C.). After thorough washing of the resin with solvent (e.g. DMF and methylene chloride), it is dried. The removal of the trityl linker is carried out with acetic acid and methylene chloride. After concentration of the solvent in vacuo, the regio- and diastereomers (6) and (7) are obtained.

The invention further relates to pharmaceuticals which contain one or more compounds of the formula I according to the invention and/or their pharmacologically tolerable salts.

The pharmaceuticals are prepared by processes known per se, which are familiar to the person skilled in the art. As pharmaceuticals, the pharmacologically active compounds according to the invention (=active compound) are either employed as such, or preferably in combination with suitable pharmaceutical auxiliaries in the form of tablets, coated tablets, capsules, suppositories, emulsions, suspensions, granules, powders, solutions or preparations having protracted release of active compound, the active compound content advantageously being 0.1 to 95%.

The person skilled in the art is familiar on the basis of his/her expert knowledge with auxiliaries which are suitable for the desired pharmaceutical formulation. In addition to solvents, gel-forming agents, suppository bases, tablet auxiliaries and other active compound carriers, it is possible to use, for example, antioxidants, dispersants, emulsifiers, antifoams, flavor corrigents, preservatives, solubilizers or colorants.

The active compounds can be administered topically, orally, parenterally or intravenously, the preferred type of administration being dependent on the disease to be treated. Oral administration is preferred.

For an oral administration form, the active compounds are mixed with the additives suitable for this purpose such as excipients, stabilizers or inert diluents and brought by means of customary methods into suitable administration forms, such as tablets, coated tablets, hard capsules, aqueous, alcoholic or oily suspensions or aqueous, alcoholic or oily solutions. Inert excipients which can be used are, for example, gum arabic, magnesia, magnesium carbonate, potassium phosphate, lactose, glucose or starch, in particular cornstarch. In this case, preparation can be carried out both as dry and as moist granules. Suitable oily excipients or solvents are vegetable or animal oils, such as sunflower oil or fish liver oil.

For subcutaneous or intravenous administration, the active compounds or their physiologically tolerable salts, if desired with the substances customary for this purpose such as solubilizers, emulsifiers or other auxiliaries, are brought into solution, suspension or emulsion. Possible solvents are, for example, water, physiological saline solution or alcohols, e.g. ethanol, propanol, glycerol, and in addition also sugar solutions such as glucose or mannitol solutions, or alternatively a mixture of various solvents.

Suitable pharmaceutical preparations for topical and local use are eye drops which contain the active compound in aqueous or oily solution. For application to the nose, aerosols and sprays, and also coarse powders, which are administered by rapid inhalation through the nostrils, and especially nasal drops which contain the active compounds in aqueous or oily solution, are suitable.

The dose of the active compound of the formula I to be administered and the frequency of administration depend on the potency and duration of action of the compound according to the invention used; and additionally also on the nature and severity of the disease to be treated and on the sex, age, weight and individual responsiveness of the mammal to be treated. On average, the recommended daily dose of a compound according to the invention in the case of a mammal weighing approximately 75 kg—primarily a human—is in the range from approximately 10 to 500 mg, preferably from approximately 25 to 250 mg, where administration, if required, can take place in several doses per day.

The compounds listed in Tables 1–5 can be prepared according to the processes described above.

TABLE 1

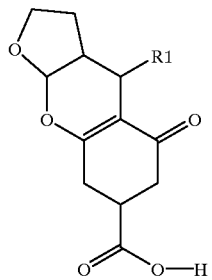

| Ex. | $R^1$ | Chem. mass |
|---|---|---|
| 1 | $-CH_2-CH_2-CH_3$ | 280.32 |
| 2 | 4-Quinolyl | 365.39 |
| 3 | $-CH_2-CH_2$-phenyl | 342.39 |
| 4 | 4-Methoxy-3-methylphenyl | 358.39 |
| 5 | 4-Trifluoromethoxyphenyl | 398.34 |
| 6 | 2,4,6-Trimethylphenyl | 356.42 |
| 7 | 4-tert-Butylphenyl | 370.45 |
| 8 | 3,5-Dimethoxyphenyl | 374.39 |
| 9 | $-CH_2-C(CH_3)_3$ | 308.38 |
| 10 | 4-Ethylphenyl | 342.39 |
| 11 | Thiophen-2-yl | 319.36 |
| 12 | -Phenyl-$CO_2-CH_3$ | 372.38 |
| 13 | 4-Phenoxyphenyl | 406.44 |
| 14 | $-C(CH_3)=CH$-phenyl-$C(CH_3)_3$ | 410.51 |
| 15 | $-CH_2-CH(CH_3)$-phenyl | 356.42 |
| 16 | $-CH(CH_3)-CH(CH_3)-C_2H_5$ | 322.40 |
| 17 | 2,5-Dimethyl-4-methoxyphenyl | 372.42 |
| 18 | 3,5-Dichloro-2-hydroxyphenyl | 399.23 |
| 19 | 3,4-(Methylenedioxy)-6-nitrophenyl | 403.35 |
| 20 | 3,5-Dimethoxy-2-methylphenyl | 388.42 |
| 21 | 3-Ethoxy-4-methoxyphenyl | 388.42 |
| 22 | 3-Ethoxy-4-phenylphenyl | 420.46 |
| 23 | $-C_{12}H_{25}$ | 406.57 |
| 24 | 2,3-Dimethyl-4-methoxyphenyl | 372.42 |
| 25 | 3-Hydroxy-4-nitrophenyl | 375.34 |
| 26 | 2-Ethoxy-3,5-dimethoxyphenyl | 418.45 |
| 27 | 3-Bromo-2,4-dimethoxyphenyl | 453.29 |
| 28 | 2,4-Dimethoxy-3-phenyl | 388.42 |
| 29 | 4-N—$(C_4H_9)$-2-phenyl | 441.57 |
| 30 | 3-Bromo-3-methoxyphenyl | 423.26 |
| 31 | 9-Anthracenyl | 414.46 |

TABLE 1-continued

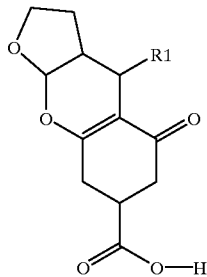

| Ex. | $R^1$ | Chem. mass |
|---|---|---|
| 32 | 2-Hydroxy-3,5-diiodophenyl | 582.13 |
| 33 | 3-Bromo-6-hydroxy-5-methoxyphenyl | 439.26 |

TABLE 2

| Ex. | $R^1$ | Chem. mass |
|---|---|---|
| 1 | $-CH_2-CH_2-CH_3$ | 294.35 |
| 2 | 4-Quinolyl | 379.41 |
| 3 | $-CH_2-CH_2$-phenyl | 356.42 |
| 4 | 4-Methoxy-3-methylphenyl | 372.42 |
| 5 | 4-Trifluoromethoxyphenyl | 412.36 |
| 6 | 2,4,6-Trimethylphenyl | 370.45 |
| 7 | 4-tert-Butylphenyl | 384.47 |
| 8 | 3,5-Dimethoxyphenyl | 388.42 |
| 9 | $-CH_2-C(CH_3)_3$ | 322.40 |
| 10 | 4-Ethylphenyl | 356.42 |
| 11 | Thiophen-2-yl | 333.39 |
| 12 | -Phenyl-$CO_2-CH_3$ | 386.40 |
| 13 | 4-Phenoxyphenyl | 420.46 |
| 14 | $-C(CH_3)=CH$-phenyl-$C(CH_3)_3$ | 424.54 |
| 15 | $-CH_2-CH(CH_3)$-phenyl | 370.45 |
| 16 | $-CH(CH_3)-CH(CH_3)-C_2H_5$ | 336.43 |
| 17 | 2,5-Dimethyl-4-methoxyphenyl | 386.45 |
| 18 | 3,5-Dichloro-2-hydroxyphenyl | 413.26 |
| 19 | 3,4-(Methylenedioxy)-6-nitrophenyl | 417.37 |
| 20 | 3,5-Dimethoxy-2-methylphenyl | 402.45 |
| 21 | 3-Ethoxy-4-methoxyphenyl | 402.45 |
| 22 | 3-Ethoxy-4-phenylphenyl | 434.49 |
| 23 | $-C_{12}H_{25}$ | 420.59 |
| 24 | 2,3-Dimethyl-4-methoxyphenyl | 386.45 |
| 25 | 3-Hydroxy-4-nitrophenyl | 389.36 |
| 26 | 2-Ethoxy-3,5-dimethoxyphenyl | 432.47 |
| 27 | 3-Bromo-2,4-dimethoxyphenyl | 467.32 |
| 28 | 2,4-Dimethoxy-3-phenyl | 402.45 |
| 29 | 4-N—$(C_4H_9)$-2-phenyl | 455.60 |
| 30 | 3-Bromo-3-methoxyphenyl | 437.29 |
| 31 | 9-Anthracenyl | 428.49 |
| 32 | 2-Hydroxy-3,5-diiodophenyl | 596.16 |
| 33 | 3-Bromo-6-hydroxy-5-methoxyphenyl | 453.29 |

TABLE 3

[Structure: chroman-one with R1, R2, R3 substituents and carboxylic acid group]

$R^2$ = hydrogen

| Ex. | $R^1$ | $R^3$ | Chem. mass |
|---|---|---|---|
| 1 | —CH₂—CH₂—CH₃ | Ethoxy | 282.34 |
| 2 | 4-Quinolyl | Ethoxy | 367.40 |
| 3 | —CH₂—CH₂-phenyl | Ethoxy | 344.41 |
| 4 | 4-Methoxy-3-methylphenyl | Ethoxy | 360.41 |
| 5 | 4-Trifluoromethoxyphenyl | Ethoxy | 400.35 |
| 6 | 2,4,6-Trimethylphenyl | Ethoxy | 358.44 |
| 7 | 4-tert-Butylphenyl | Ethoxy | 372.46 |
| 8 | 3,5-Dimethoxyphenyl | Ethoxy | 376.41 |
| 9 | —CH₂—C(CH₃)₃ | Ethoxy | 310.39 |
| 10 | 4-Ethylphenyl | Ethoxy | 344.41 |
| 11 | Thiophen-2-yl | Ethoxy | 321.38 |
| 12 | -Phenyl-CO₂—CH₃ | Ethoxy | 374.39 |
| 13 | 4-Phenoxyphenyl | Ethoxy | 408.45 |
| 14 | —C(CH₃)=CH-phenyl-C(CH₃)₃ | Ethoxy | 412.53 |
| 15 | —CH₂—CH(CH₃)-phenyl | Ethoxy | 358.44 |
| 16 | —CH(CH₃)—CH(CH₃)—C₂H₅ | Ethoxy | 324.42 |
| 17 | 2,5-Dimethyl-4-methoxy-phenyl | Ethoxy | 374.44 |
| 18 | 3,5-Dichloro-2-hydroxyphenyl | Ethoxy | 401.24 |
| 19 | 3,4-(Methylenedioxy)-6-nitro-phenyl | Ethoxy | 405.36 |
| 20 | 3,5-Dimethoxy-2-methyl-phenyl | Ethoxy | 390.44 |
| 21 | 3-Ethoxy-4-methoxyphenyl | Ethoxy | 390.44 |
| 22 | 3-Ethoxy-4-phenylphenyl | Ethoxy | 422.48 |
| 23 | —C₁₂H₂₅ | Ethoxy | 408.58 |
| 24 | 2,3-Dimethyl-4-methoxy-phenyl | Ethoxy | 374.44 |
| 25 | 3-Hydroxy-4-nitrophenyl | Ethoxy | 377.35 |
| 26 | 2-Ethoxy-3,5-dimethoxy-phenyl | Ethoxy | 420.46 |
| 27 | 3-Bromo-2,4-dimethoxy-phenyl | Ethoxy | 455.30 |
| 28 | 2,4-Dimethoxy-3-phenyl | Ethoxy | 390.44 |
| 29 | 4-N—(C₄H₉)-2-phenyl | Ethoxy | 443.59 |
| 30 | 3-Bromo-3-methoxyphenyl | Ethoxy | 425.28 |
| 31 | 9-Anthracenyl | Ethoxy | 416.48 |
| 32 | 2-Hydroxy-3,5-diiodophenyl | Ethoxy | 584.15 |
| 33 | 3-Bromo-6-hydroxy-5-methoxyphenyl | Ethoxy | 441.28 |
| 34 | —CH₂—CH₂—CH₃ | Phenylmercapto | 346.45 |
| 35 | 4-Quinolyl | Phenylmercapto | 431.51 |
| 36 | —CH₂—CH₂-phenyl | Phenylmercapto | 408.52 |
| 37 | 4-Methoxy-3-methylphenyl | Phenylmercapto | 424.52 |
| 38 | 4-Trifluoromethoxyphenyl | Phenylmercapto | 464.46 |
| 39 | 2,4,6-Trimethylphenyl | Phenylmercapto | 422.55 |
| 40 | 4-tert-Butylphenyl | Phenylmercapto | 436.57 |
| 41 | 3,5-Dimethoxyphenyl | Phenylmercapto | 440.52 |
| 42 | —CH₂—C(CH₃)₃ | Phenylmercapto | 374.50 |
| 43 | 4-Ethylphenyl | Phenylmercapto | 408.52 |
| 44 | Thiophen-2-yl | Phenylmercapto | 385.49 |
| 45 | C₆H₄—CO₂—CH₃ | Phenylmercapto | 438.50 |
| 46 | 4-Phenoxyphenyl | Phenylmercapto | 472.56 |
| 47 | —C(CH₃)=CH—C₆H₄—C(CH₃)₃ | Phenylmercapto | 476.64 |
| 48 | —CH₂—CH(CH₃)—C₆H₅ | Phenylmercapto | 422.55 |
| 49 | —CH(CH₃)—CH(CH₃)—C₂H₅ | Phenylmercapto | 388.53 |
| 50 | 2,5-Dimethyl-4-methoxy-phenyl | Phenylmercapto | 438.55 |
| 51 | 3,5-Dichloro-2-hydroxyphenyl | Phenylmercapto | 465.36 |

TABLE 3-continued

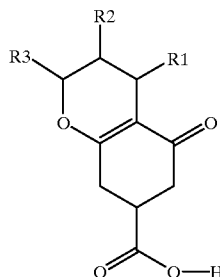

R² = hydrogen

| Ex. | R¹ | R³ | Chem. mass |
|---|---|---|---|
| 52 | 3,4-(Methylenedioxy)-6-nitro-phenyl | Phenylmercapto | 469.47 |
| 53 | 3,5-Dimethoxy-2-methyl-phenyl | Phenylmercapto | 454.55 |
| 54 | 3-Ethoxy-4-methoxyphenyl | Phenylmercapto | 454.55 |
| 55 | 3-Ethoxy-4-phenylphenyl | Phenylmercapto | 486.59 |
| 56 | —$C_{12}H_{25}$ | Phenylmercapto | 472.69 |
| 57 | 2,3-Dimethyl-4-methoxy-phenyl | Phenylmercapto | 438.55 |
| 58 | 3-Hydroxy-4-nitrophenyl | Phenylmercapto | 441.46 |
| 59 | 2-Ethoxy-3,5-dimethoxy-phenyl | Phenylmercapto | 484.57 |
| 60 | 3-Bromo-2,4-dimethoxy-phenyl | Phenylmercapto | 519.42 |
| 61 | 2,4-Dimethoxy-3-phenyl | Phenylmercapto | 454.55 |
| 62 | 4-N—($C_4H_9$)-2-phenyl | Phenylmercapto | 507.70 |
| 63 | 3-Bromo-3-methoxyphenyl | Phenylmercapto | 489.39 |
| 64 | 9-Anthracenyl | Phenylmercapto | 480.59 |
| 65 | 2-Hydroxy-3,5-diiodophenyl | Phenylmercapto | 648.26 |
| 66 | 3-Bromo-6-hydroxy-5-methoxyphenyl | Phenylmercapto | 505.39 |
| 67 | —$CH_2$—$CH_2$—$CH_3$ | 2-Chloroethoxy | 316.78 |
| 68 | 4-Quinolyl | 2-Chloroethoxy | 401.85 |
| 69 | —$CH_2$—$CH_2$-phenyl | 2-Chloroethoxy | 378.85 |
| 70 | 4-Methoxy-3-methylphenyl | 2-Chloroethoxy | 394.85 |
| 71 | 4-Trifluoromethoxyphenyl | 2-Chloroethoxy | 434.80 |
| 72 | 2,4,6-Trimethylphenyl | 2-Chloroethoxy | 392.88 |
| 73 | 4-tert-Butylphenyl | 2-Chloroethoxy | 406.91 |
| 74 | 3,5-Dimethoxyphenyl | 2-Chloroethoxy | 410.85 |
| 75 | —$CH_2$—$C(CH_3)_3$ | 2-Chloroethoxy | 344.84 |
| 76 | 4-Ethylphenyl | 2-Chloroethoxy | 378.85 |
| 77 | Thiophen-2-yl | 2-Chloroethoxy | 355.82 |
| 78 | -Phenyl-$CO_2$—$CH_3$ | 2-Chloroethoxy | 408.84 |
| 79 | 4-Phenoxyphenyl | 2-Chloroethoxy | 442.90 |
| 80 | —$C(CH_3)$=CH-phenyl-$C(CH_3)_3$ | 2-Chloroethoxy | 446.97 |
| 81 | —$CH_2$—$CH(CH_3)$-phenyl | 2-Chloroethoxy | 392.88 |
| 82 | —$CH(CH_3)$—$CH(CH_3)$—$C_2H_5$ | 2-Chloroethoxy | 358.86 |
| 83 | 2,5-Dimethyl-4-methoxy-phenyl | 2-Chloroethoxy | 408.88 |
| 84 | 3,5-Dichloro-2-hydroxyphenyl | 2-Chloroethoxy | 435.69 |
| 85 | 3,4-(Methylenedioxy)-6-nitro-phenyl | 2-Chloroethoxy | 439.81 |
| 86 | 3,5-Dimethoxy-2-methyl-phenyl | 2-Chloroethoxy | 424.88 |
| 87 | 3-Ethoxy-4-methoxyphenyl | 2-Chloroethoxy | 424.88 |
| 88 | 3-Ethoxy-4-phenylphenyl | 2-Chloroethoxy | 456.93 |
| 89 | —$C_{12}H_{25}$ | 2-Chloroethoxy | 443.03 |
| 90 | 2,3-Dimethyl-4-methoxy-phenyl | 2-Chloroethoxy | 408.88 |
| 91 | 3-Hydroxy-4-nitrophenyl | 2-Chloroethoxy | 411.80 |
| 92 | 2-Ethoxy-3,5-dimethoxy-phenyl | 2-Chloroethoxy | 454.91 |
| 93 | 3-Bromo-2,4-dimethoxy-phenyl | 2-Chloroethoxy | 489.75 |
| 94 | 2,4-Dimethoxy-3-phenyl | 2-Chloroethoxy | 424.88 |
| 95 | 4-N—($C_4H_9$)-2-phenyl | 2-Chloroethoxy | 478.03 |
| 96 | 3-Bromo-3-methoxyphenyl | 2-Chloroethoxy | 459.72 |
| 97 | 9-Anthracenyl | 2-Chloroethoxy | 450.92 |
| 98 | 2-Hydroxy-3,5-diiodophenyl | 2-Chloroethoxy | 618.59 |

TABLE 3-continued

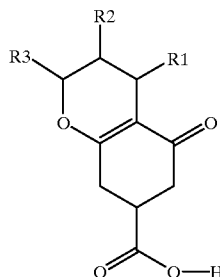

R² = hydrogen

| Ex. | R¹ | R³ | Chem. mass |
|---|---|---|---|
| 99 | 3-Bromo-6-hydroxy-5-methoxyphenyl | 2-Chloroethoxy | 475.72 |
| 100 | —CH₂—CH₂—CH₃ | —O—CH₂—CH(CH₃)₂ | 310.39 |
| 101 | 4-Quinolyl | —O—CH₂—CH(CH₃)₂ | 395.46 |
| 102 | —CH₂—CH₂-phenyl | —O—CH₂—CH(CH₃)₂ | 372.46 |
| 103 | 4-Methoxy-3-methylphenyl | —O—CH₂—CH(CH₃)₂ | 388.46 |
| 104 | 4-Trifluoromethoxyphenyl | —O—CH₂—CH(CH₃)₂ | 428.41 |
| 105 | 2,4,6-Trimethylphenyl | —O—CH₂—CH(CH₃)₂ | 386.49 |
| 106 | 4-tert-Butylphenyl | —O—CH₂—CH(CH₃)₂ | 400.52 |
| 107 | 3,5-Dimethoxyphenyl | —O—CH₂—CH(CH₃)₂ | 404.46 |
| 108 | —CH₂—C(CH₃)₃ | —O—CH₂—CH(CH₃)₂ | 338.45 |
| 109 | 4-Ethylphenyl | —O—CH₂—CH(CH₃)₂ | 372.46 |
| 110 | Thiophen-2-yl | —O—CH₂—CH(CH₃)₂ | 349.43 |
| 111 | -Phenyl-CO₂—CH₃ | —O—CH₂—CH(CH₃)₂ | 402.45 |
| 112 | 4-Phenoxyphenyl | —O—CH₂—CH(CH₃)₂ | 436.51 |
| 113 | —C(CH₃)=CH-phenyl-C(CH₃)₃ | —O—CH₂—CH(CH₃)₂ | 440.58 |
| 114 | —CH₂—CH(CH₃)-phenyl | —O—CH₂—CH(CH₃)₂ | 386.49 |
| 115 | —CH(CH₃)—CH(CH₃)—C₂H₅ | —O—CH₂—CH(CH₃)₂ | 352.47 |
| 116 | 2,5-Dimethyl-4-methoxy-phenyl | —O—CH₂—CH(CH₃)₂ | 402.49 |
| 117 | 3,5-Dichloro-2-hydroxyphenyl | —O—CH₂—CH(CH₃)₂ | 429.30 |
| 118 | 3,4-(Methylenedioxy)-6-nitro-phenyl | —O—CH₂—CH(CH₃)₂ | 433.42 |
| 119 | 3,5-Dimethoxy-2-methyl-phenyl | —O—CH₂—CH(CH₃)₂ | 418.49 |
| 120 | 3-Ethoxy-4-methoxyphenyl | —O—CH₂—CH(CH₃)₂ | 418.49 |
| 121 | 3-Ethoxy-4-phenylphenyl | —O—CH₂—CH(CH₃)₂ | 450.53 |
| 122 | —C₁₂H₂₅ | —O—CH₂—CH(CH₃)₂ | 436.63 |
| 123 | 2,3-Dimethyl-4-methoxy-phenyl | —O—CH₂—CH(CH₃)₂ | 402.49 |
| 124 | 3-Hydroxy-4-nitrophenyl | —O—CH₂—CH(CH₃)₂ | 405.41 |
| 125 | 2-Ethoxy-3,5-dimethoxy-phenyl | —O—CH₂—CH(CH₃)₂ | 448.52 |
| 126 | 3-Bromo-2,4-dimethoxy-phenyl | —O—CH₂—CH(CH₃)₂ | 483.36 |
| 127 | 2,4-Dimethoxy-3-phenyl | —O—CH₂—CH(CH₃)₂ | 418.49 |
| 128 | 4-N—(C₄H₉)-2-phenyl | —O—CH₂—CH(CH₃)₂ | 471.64 |
| 129 | 3-Bromo-3-methoxyphenyl | —O—CH₂—CH(CH₃)₂ | 453.33 |
| 130 | 9-Anthracenyl | —O—CH₂—CH(CH₃)₂ | 444.53 |
| 131 | 2-Hydroxy-3,5-diiodophenyl | —O—CH₂—CH(CH₃)₂ | 612.20 |
| 132 | 3-Bromo-6-hydroxy-5-methoxyphenyl | —O—CH₂—CH(CH₃)₂ | 469.33 |
| 133 | —CH₂—CH₂—CH₃ | n-Butyloxy | 310.39 |
| 134 | 4-Quinolyl | n-Butyloxy | 395.46 |
| 135 | —CH₂—CH₂-phenyl | n-Butyloxy | 372.46 |
| 136 | 4-Methoxy-3-methylphenyl | n-Butyloxy | 388.46 |
| 137 | 4-Trifluoromethoxyphenyl | n-Butyloxy | 428.41 |
| 138 | 2,4,6-Trimethylphenyl | n-Butyloxy | 386.49 |
| 139 | 4-tert-Butylphenyl | n-Butyloxy | 400.52 |
| 140 | 3,5-Dimethoxyphenyl | n-Butyloxy | 404.46 |
| 141 | —CH₂—C(CH₃)₃ | n-Butyloxy | 338.45 |
| 142 | 4-Ethylphenyl | n-Butyloxy | 372.46 |
| 143 | Thiophen-2-yl | n-Butyloxy | 349.43 |
| 144 | -Phenyl-CO₂—CH₃ | n-Butyloxy | 402.45 |
| 145 | 4-Phenoxyphenyl | n-Butyloxy | 436.51 |
| 146 | —C(CH₃)=CH-phenyl-C(CH₃)₃ | n-Butyloxy | 440.58 |
| 147 | —CH₂—CH(CH₃)-phenyl | n-Butyloxy | 386.49 |
| 148 | —CH(CH₃)—CH(CH₃)—C₂H₅ | n-Butyloxy | 352.47 |

TABLE 3-continued

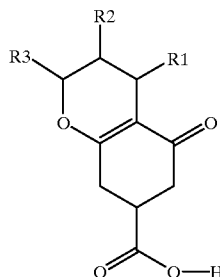

R² = hydrogen

| Ex. | R¹ | R³ | Chem. mass |
|---|---|---|---|
| 149 | 2,5-Dimethyl-4-methoxy-phenyl | n-Butyloxy | 402.49 |
| 150 | 3,5-Dichloro-2-hydroxyphenyl | n-Butyloxy | 429.30 |
| 151 | 3,4-(Methylenedioxy)-6-nitro-phenyl | n-Butyloxy | 433.42 |
| 152 | 3,5-Dimethoxy-2-methyl-phenyl | n-Butyloxy | 418.49 |
| 153 | 3-Ethoxy-4-methoxyphenyl | n-Butyloxy | 418.49 |
| 154 | 3-Ethoxy-4-phenylphenyl | n-Butyloxy | 450.53 |
| 155 | —$C_{12}H_{25}$ | n-Butyloxy | 436.63 |
| 156 | 2,3-Dimethyl-4-methoxy-phenyl | n-Butyloxy | 402.49 |
| 157 | 3-Hydroxy-4-nitrophenyl | n-Butyloxy | 405.41 |
| 158 | 2-Ethoxy-3,5-dimethoxy-phenyl | n-Butyloxy | 448.52 |
| 159 | 3-Bromo-2,4-dimethoxy-phenyl | n-Butyloxy | 483.36 |
| 160 | 2,4-Dimethoxy-3-phenyl | n-Butyloxy | 418.49 |
| 161 | 4-N—($C_4H_9$)-2-phenyl | n-Butyloxy | 471.64 |
| 162 | 3-Bromo-3-methoxyphenyl | n-Butyloxy | 453.33 |
| 163 | 9-Anthracenyl | n-Butyloxy | 444.53 |
| 164 | 2-Hydroxy-3,5-diiodophenyl | n-Butyloxy | 612.20 |
| 165 | 3-Bromo-6-hydroxy-5-methoxyphenyl | n-Butyloxy | 469.33 |
| 166 | —$CH_2$—$CH_2$—$CH_3$ | —O—$(CH_2)_4$—OH | 326.39 |
| 167 | 4-Quinolyl | —O—$(CH_2)_4$—OH | 411.46 |
| 168 | —$CH_2$—$CH_2$-phenyl | —O—$(CH_2)_4$—OH | 388.46 |
| 169 | 4-Methoxy-3-methylphenyl | —O—$(CH_2)_4$—OH | 404.46 |
| 170 | 4-Trifluoromethoxyphenyl | —O—$(CH_2)_4$—OH | 444.41 |
| 171 | 2,4,6-Trimethylphenyl | —O—$(CH_2)_4$—OH | 402.49 |
| 172 | 4-tert-Butylphenyl | —O—$(CH_2)_4$—OH | 416.52 |
| 173 | 3,5-Dimethoxyphenyl | —O—$(CH_2)_4$—OH | 420.46 |
| 174 | —$CH_2$—$C(CH_3)_3$ | —O—$(CH_2)_4$—OH | 354.45 |
| 175 | 4-Ethylphenyl | —O—$(CH_2)_4$—OH | 388.46 |
| 176 | Thiophen-2-yl | —O—$(CH_2)_4$—OH | 365.43 |
| 177 | -Phenyl-$CO_2$—$CH_3$ | —O—$(CH_2)_4$—OH | 418.45 |
| 178 | 4-Phenoxyphenyl | —O—$(CH_2)_4$—OH | 452.51 |
| 179 | —$C(CH_3)$=CH-phenyl-$C(CH_3)_3$ | —O—$(CH_2)_4$—OH | 456.58 |
| 180 | —$CH_2$—$CH(CH_3)$-phenyl | —O—$(CH_2)_4$—OH | 402.49 |
| 181 | —$CH(CH_3)$—$CH(CH_3)$—$C_2H_5$ | —O—$(CH_2)_4$—OH | 368.47 |
| 182 | 2,5-Dimethyl-4-methoxy-phenyl | —O—$(CH_2)_4$—OH | 418.49 |
| 183 | 3,5-Dichloro-2-hydroxyphenyl | —O—$(CH_2)_4$—OH | 445.30 |
| 184 | 3,4-(Methylenedioxy)-6-nitro-phenyl | —O—$(CH_2)_4$—OH | 449.42 |
| 185 | 3,5-Dimethoxy-2-methyl-phenyl | —O—$(CH_2)_4$—OH | 434.49 |
| 186 | 3-Ethoxy-4-methoxyphenyl | —O—$(CH_2)_4$—OH | 434.49 |
| 187 | 3-Ethoxy-4-phenylphenyl | —O—$(CH_2)_4$—OH | 466.53 |
| 188 | —$C_{12}H_{25}$ | —O—$(CH_2)_4$—OH | 452.63 |
| 189 | 2,3-Dimethyl-4-methoxy-phenyl | —O—$(CH_2)_4$—OH | 418.49 |
| 190 | 3-Hydroxy-4-nitrophenyl | —O—$(CH_2)_4$—OH | 421.41 |
| 191 | 2-Ethoxy-3,5-dimethoxy-phenyl | —O—$(CH_2)_4$—OH | 464.52 |
| 192 | 3-Bromo-2,4-dimethoxy-phenyl | —O—$(CH_2)_4$—OH | 499.36 |
| 193 | 2,4-Dimethoxy-3-phenyl | —O—$(CH_2)_4$—OH | 434.49 |
| 194 | 4-N—($C_4H_9$)-2-phenyl | —O—$(CH_2)_4$—OH | 487.64 |
| 195 | 3-Bromo-3-methoxyphenyl | —O—$(CH_2)_4$—OH | 469.33 |

TABLE 3-continued

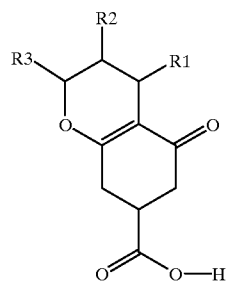

R² = hydrogen

| Ex. | R¹ | R³ | Chem. mass |
|---|---|---|---|
| 196 | 9-Anthracenyl | —O—(CH₂)₄—OH | 460.53 |
| 197 | 2-Hydroxy-3,5-diiodophenyl | —O—(CH₂)₄—OH | 628.20 |
| 198 | 3-Bromo-6-hydroxy-5-methoxyphenyl | —O—(CH₂)₄—OH | 485.33 |
| 199 | —CH₂—CH₂—CH₃ | —O—(CH₂)₃—NH₂ | 311.38 |
| 200 | 4-Quinolyl | —O—(CH₂)₃—NH₂ | 396.45 |
| 201 | —CH₂—CH₂-phenyl | —O—(CH₂)₃—NH₂ | 373.45 |
| 202 | 4-Methoxy-3-methylphenyl | —O—(CH₂)₃—NH₂ | 389.45 |
| 203 | 4-Trifluoromethoxyphenyl | —O—(CH₂)₃—NH₂ | 429.40 |
| 204 | 2,4,6-Trimethylphenyl | —O—(CH₂)₃—NH₂ | 387.48 |
| 205 | 4-tert-Butylphenyl | —O—(CH₂)₃—NH₂ | 401.51 |
| 206 | 3,5-Dimethoxyphenyl | —O—(CH₂)₃—NH₂ | 405.45 |
| 207 | —CH₂—C(CH₃)₃ | —O—(CH₂)₃—NH₂ | 339.43 |
| 208 | 4-Ethylphenyl | —O—(CH₂)₃—NH₂ | 373.45 |
| 209 | Thiophen-2-yl | —O—(CH₂)₃—NH₂ | 350.42 |
| 210 | -Phenyl-CO₂—CH₃ | —O—(CH₂)₃—NH₂ | 403.43 |
| 211 | 4-Phenoxyphenyl | —O—(CH₂)₃—NH₂ | 437.50 |
| 212 | —C(CH₃)=CH-phenyl-C(CH₃)₃ | —O—(CH₂)₃—NH₂ | 441.57 |
| 213 | —CH₂—CH(CH₃)-phenyl | —O—(CH₂)₃—NH₂ | 387.48 |
| 214 | —CH(CH₃)—CH(CH₃)—C₂H₅ | —O—(CH₂)₃—NH₂ | 353.46 |
| 215 | 2,5-Dimethyl-4-methoxyphenyl | —O—(CH₂)₃—NH₂ | 403.48 |
| 216 | 3,5-Dichloro-2-hydroxyphenyl | —O—(CH₂)₃—NH₂ | 430.29 |
| 217 | 3,4-(Methylenedioxy)-6-nitrophenyl | —O—(CH₂)₃—NH₂ | 434.40 |
| 218 | 3,5-Dimethoxy-2-methylphenyl | —O—(CH₂)₃—NH₂ | 419.48 |
| 219 | 3-Ethoxy-4-methoxyphenyl | —O—(CH₂)₃—NH₂ | 419.48 |
| 220 | 3-Ethoxy-4-phenylphenyl | —O—(CH₂)₃—NH₂ | 451.52 |
| 221 | —C₁₂H₂₅ | —O—(CH₂)₃—NH₂ | 437.62 |
| 222 | 2,3-Dimethyl-4-methoxyphenyl | —O—(CH₂)₃—NH₂ | 403.48 |
| 223 | 3-Hydroxy-4-nitrophenyl | —O—(CH₂)₃—NH₂ | 406.39 |
| 224 | 2-Ethoxy-3,5-dimethoxyphenyl | —O—(CH₂)₃—NH₂ | 449.50 |
| 225 | 3-Bromo-2,4-dimethoxyphenyl | —O—(CH₂)₃—NH₂ | 484.35 |
| 226 | 2,4-Dimethoxy-3-phenyl | —O—(CH₂)₃—NH₂ | 419.48 |
| 227 | 4-N—(C₄H₉)-2-phenyl | —O—(CH₂)₃—NH₂ | 472.63 |
| 228 | 3-Bromo-3-methoxyphenyl | —O—(CH₂)₃—NH₂ | 454.32 |
| 229 | 9-Anthracenyl | —O—(CH₂)₃—NH₂ | 445.52 |
| 230 | 2-Hydroxy-3,5-diiodophenyl | —O—(CH₂)₃—NH₂ | 613.19 |
| 231 | 3-Bromo-6-hydroxy-5-methoxyphenyl | —O—(CH₂)₃—NH₂ | 470.32 |
| 232 | —CH₂—CH₂—CH₃ | —O-cyclohexyl | 336.43 |
| 233 | 4-Quinolyl | —O-cyclohexyl | 421.50 |
| 234 | —CH₂—CH₂-phenyl | —O-cyclohexyl | 398.50 |
| 235 | 4-Methoxy-3-methylphenyl | —O-cyclohexyl | 414.50 |
| 236 | 4-Trifluoromethoxyphenyl | —O-cyclohexyl | 454.45 |
| 237 | 2,4,6-Trimethylphenyl | —O-cyclohexyl | 412.53 |
| 238 | 4-tert-Butylphenyl | —O-cyclohexyl | 426.56 |
| 239 | 3,5-Dimethoxyphenyl | —O-cyclohexyl | 430.50 |
| 240 | —CH₂—C(CH₃)₃ | —O-cyclohexyl | 364.48 |
| 241 | 4-Ethylphenyl | —O-cyclohexyl | 398.50 |
| 242 | Thiophen-2-yl | —O-cyclohexyl | 375.47 |
| 243 | C₆H₄—CO₂—CH₃ | —O-cyclohexyl | 428.48 |
| 244 | 4-Phenoxyphenyl | —O-cyclohexyl | 462.55 |
| 245 | —C(CH₃)=CH—C₆H₄—C(CH₃)₃ | —O-cyclohexyl | 466.62 |
| 246 | —CH₂—CH(CH₃)—C₆H₅ | —O-cyclohexyl | 412.53 |

TABLE 3-continued

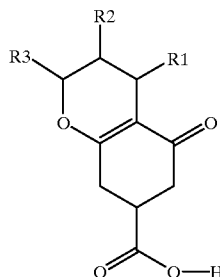

R² = hydrogen

| Ex. | R¹ | R³ | Chem. mass |
|---|---|---|---|
| 247 | —CH(CH₃)—CH(CH₃)—C₂H₅ | —O-cyclohexyl | 378.51 |
| 248 | 2,5-Dimethyl-4-methoxyphenyl | —O-cyclohexyl | 428.53 |
| 249 | 3,5-Dichloro-2-hydroxyphenyl | —O-cyclohexyl | 455.34 |
| 250 | 3,4-(Methylenedioxy)-6-nitrophenyl | —O-cyclohexyl | 459.46 |
| 251 | 3,5-Dimethoxy-2-methylphenyl | —O-cyclohexyl | 444.53 |
| 252 | 3-Ethoxy-4-methoxyphenyl | —O-cyclohexyl | 444.53 |
| 253 | 3-Ethoxy-4-phenylphenyl | —O-cyclohexyl | 476.57 |
| 254 | —C₁₂H₂₅ | —O-cyclohexyl | 462.67 |
| 255 | 2,3-Dimethyl-4-methoxyphenyl | —O-cyclohexyl | 428.53 |
| 256 | 3-Hydroxy-4-nitrophenyl | —O-cyclohexyl | 431.44 |
| 257 | 2-Ethoxy-3,5-dimethoxyphenyl | —O-cyclohexyl | 474.55 |
| 258 | 3-Bromo-2,4-dimethoxyphenyl | —O-cyclohexyl | 509.40 |
| 259 | 2,4-Dimethoxy-3-phenyl | —O-cyclohexyl | 444.53 |
| 260 | 4-N—(C₄H₉)-2-phenyl | —O-cyclohexyl | 497.68 |
| 261 | 3-Bromo-3-methoxyphenyl | —O-cyclohexyl | 479.37 |
| 262 | 9-Anthracenyl | —O-cyclohexyl | 470.57 |
| 263 | 2-Hydroxy-3,5-diiodophenyl | —O-cyclohexyl | 638.24 |
| 264 | 3-Bromo-6-hydroxy-5-methoxyphenyl | —O-cyclohexyl | 495.37 |
| 265 | —CH₂—CH₂—CH₃ | —O—(CH₂)₆—OH | 338.45 |
| 266 | 4-Quinolyl | —O—(CH₂)₆—OH | 423.51 |
| 267 | —CH₂—CH₂-phenyl | —O—(CH₂)₆—OH | 400.52 |
| 268 | 4-Methoxy-3-methylphenyl | —O—(CH₂)₆—OH | 416.52 |
| 269 | 4-Trifluoromethoxyphenyl | —O—(CH₂)₆—OH | 456.46 |
| 270 | 2,4,6-Trimethylphenyl | —O—(CH₂)₆—OH | 414.54 |
| 271 | 4-tert-Butylphenyl | —O—(CH₂)₆—OH | 428.57 |
| 272 | 3,5-Dimethoxyphenyl | —O—(CH₂)₆—OH | 432.52 |
| 273 | —CH₂—C(CH₃)₃ | —O—(CH₂)₆—OH | 366.50 |
| 274 | 4-Ethylphenyl | —O—(CH₂)₆—OH | 400.52 |
| 275 | Thiophen-2-yl | —O—(CH₂)₆—OH | 377.48 |
| 276 | -Phenyl-CO₂—CH₃ | —O—(CH₂)₆—OH | 430.50 |
| 277 | 4-Phenoxyphenyl | —O—(CH₂)₆—OH | 464.56 |
| 278 | —C(CH₃)=CH-phenyl-C(CH₃)₃ | —O—(CH₂)₆—OH | 468.64 |
| 279 | —CH₂—CH(CH₃)-phenyl | —O—(CH₂)₆—OH | 414.54 |
| 280 | —CH(CH₃)—CH(CH₃)—C₂H₅ | —O—(CH₂)₆—OH | 380.53 |
| 281 | 2,5-Dimethyl-4-methoxyphenyl | —O—(CH₂)₆—OH | 430.54 |
| 282 | 3,5-Dichloro-2-hydroxyphenyl | —O—(CH₂)₆—OH | 457.35 |
| 283 | 3,4-(Methylenedioxy)-6-nitrophenyl | —O—(CH₂)₆—OH | 461.47 |
| 284 | 3,5-Dimethoxy-2-methylphenyl | —O—(CH₂)₆—OH | 446.54 |
| 285 | 3-Ethoxy-4-methoxyphenyl | —O—(CH₂)₆—OH | 446.54 |
| 286 | 3-Ethoxy-4-phenylphenyl | —O—(CH₂)₆—OH | 478.59 |
| 287 | —C₁₂H₂₅ | —O—(CH₂)₆—OH | 464.69 |
| 288 | 2,3-Dimethyl-4-methoxyphenyl | —O—(CH₂)₆—OH | 430.54 |
| 289 | 3-Hydroxy-4-nitrophenyl | —O—(CH₂)₆—OH | 433.46 |
| 290 | 2-Ethoxy-3,5-dimethoxyphenyl | —O—(CH₂)₆—OH | 476.57 |
| 291 | 3-Bromo-2,4-dimethoxyphenyl | —O—(CH₂)₆—OH | 511.41 |
| 292 | 2,4-Dimethoxy-3-phenyl | —O—(CH₂)₆—OH | 446.54 |

TABLE 3-continued

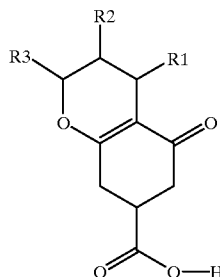

R² = hydrogen

| Ex. | R¹ | R³ | Chem. mass |
|---|---|---|---|
| 293 | 4-N—(C₄H₉)-2-phenyl | —O—(CH₂)₆—OH | 499.69 |
| 294 | 3-Bromo-3-methoxyphenyl | —O—(CH₂)₆—OH | 481.39 |
| 295 | 9-Anthracenyl | —O—(CH₂)₆—OH | 472.58 |
| 296 | 2-Hydroxy-3,5-diiodophenyl | —O—(CH₂)₆—OH | 640.26 |
| 297 | 3-Bromo-6-hydroxy-5-methoxyphenyl | —O—(CH₂)₆—OH | 497.39 |
| 298 | —CH₂—CH₂—CH₃ | —O—CH₂—CH(C₂H₅)—(CH₂)₃—CH₃ | 366.50 |
| 299 | 4-Quinolyl | —O—CH₂—CH(C₂H₅)—(CH₂)₃—CH₃ | 451.57 |
| 300 | —CH₂—CH₂-phenyl | —O—CH₂—CH(C₂H₅)—(CH₂)₃—CH₃ | 428.57 |
| 301 | 4-Methoxy-3-methylphenyl | —O—CH₂—CH(C₂H₅)—(CH₂)₃—CH₃ | 444.57 |
| 302 | 4-Trifluoromethoxyphenyl | —O—CH₂—CH(C₂H₅)—(CH₂)₃—CH₃ | 484.52 |
| 303 | 2,4,6-Trimethylphenyl | —O—CH₂—CH(C₂H₅)—(CH₂)₃—CH₃ | 442.60 |
| 304 | 4-tert-Butylphenyl | —O—CH₂—CH(C₂H₅)—(CH₂)₃—CH₃ | 456.63 |
| 305 | 3,5-Dimethoxyphenyl | —O—CH₂—CH(C₂H₅)—(CH₂)₃—CH₃ | 460.57 |
| 306 | —CH₂—C(CH₃)₃ | —O—CH₂—CH(C₂H₅)—(CH₂)₃—CH₃ | 394.55 |
| 307 | 4-Ethylphenyl | —O—CH₂—CH(C₂H₅)—(CH₂)₃—CH₃ | 428.57 |
| 308 | Thiophen-2-yl | —O—CH₂—CH(C₂H₅)—(CH₂)₃—CH₃ | 405.54 |
| 309 | -Phenyl-CO₂—CH₃ | —O—CH₂—CH(C₂H₅)—(CH₂)₃—CH₃ | 458.55 |
| 310 | 4-Phenoxyphenyl | —O—CH₂—CH(C₂H₅)—(CH₂)₃—CH₃ | 492.62 |
| 311 | —C(CH₃)=CH-phenyl-C(CH₃)₃ | —O—CH₂—CH(C₂H₅)—(CH₂)₃—CH₃ | 496.69 |
| 312 | —CH₂—CH(CH₃)-phenyl | —O—CH₂—CH(C₂H₅)—(CH₂)₃—CH₃ | 442.60 |
| 313 | —CH(CH₃)—CH(CH₃)—C₂H₅ | —O—CH₂—CH(C₂H₅)—(CH₂)₃—CH₃ | 408.58 |
| 314 | 2,5-Dimethyl-4-methoxy-phenyl | —O—CH₂—CH(C₂H₅)—(CH₂)₃—CH₃ | 458.60 |
| 315 | 3,5-Dichloro-2-hydroxyphenyl | —O—CH₂—CH(C₂H₅)—(CH₂)₃—CH₃ | 485.41 |
| 316 | 3,4-(Methylenedioxy)-6-nitro-phenyl | —O—CH₂—CH(C₂H₅)—(CH₂)₃—CH₃ | 489.52 |
| 317 | 3,5-Dimethoxy-2-methyl-phenyl | —O—CH₂—CH(C₂H₅)—(CH₂)₃—CH₃ | 474.60 |
| 318 | 3-Ethoxy-4-methoxyphenyl | —O—CH₂—CH(C₂H₅)—(CH₂)₃—CH₃ | 474.60 |
| 319 | 3-Ethoxy-4-phenylphenyl | —O—CH₂—CH(C₂H₅)—(CH₂)₃—CH₃ | 506.64 |
| 320 | —C₁₂H₂₅ | —O—CH₂—CH(C₂H₅)—(CH₂)₃—CH₃ | 492.74 |
| 321 | 2,3-Dimethyl-4-methoxy-phenyl | —O—CH₂—CH(C₂H₅)—(CH₂)₃—CH₃ | 458.60 |
| 322 | 3-Hydroxy-4-nitrophenyl | —O—CH₂—CH(C₂H₅)—(CH₂)₃—CH₃ | 461.51 |
| 323 | 2-Ethoxy-3,5-dimethoxy-phenyl | —O—CH₂—CH(C₂H₅)—(CH₂)₃—CH₃ | 504.62 |
| 324 | 3-Bromo-2,4-dimethoxy-phenyl | —O—CH₂—CH(C₂H₅)—(CH₂)₃—CH₃ | 539.47 |
| 325 | 2,4-Dimethoxy-3-phenyl | —O—CH₂—CH(C₂H₅)—(CH₂)₃—CH₃ | 474.60 |
| 326 | 4-N—(C₄H₉)₂-phenyl | —O—CH₂—CH(C₂H₅)—(CH₂)₃—CH₃ | 527.75 |
| 327 | 3-Bromo-3-methoxyphenyl | —O—CH₂—CH(C₂H₅)—(CH₂)₃—CH₃ | 509.44 |
| 328 | 9-Anthracenyl | —O—CH₂—CH(C₂H₅)—(CH₂)₃—CH₃ | 500.64 |
| 329 | 2-Hydroxy-3,5-diiodophenyl | —O—CH₂—CH(C₂H₅)—(CH₂)₃—CH₃ | 668.31 |
| 330 | 3-Bromo-6-hydroxy-5-methoxyphenyl | —O—CH₂—CH(C₂H₅)—(CH₂)₃—CH₃ | 525.44 |
| 331 | —CH₂—CH₂—CH₃ | t-Butyloxy | 310.39 |
| 332 | 4-Quinolyl | t-Butyloxy | 395.46 |
| 333 | —CH₂—CH₂-phenyl | t-Butyloxy | 372.46 |
| 334 | 4-Methoxy-3-methylphenyl | t-Butyloxy | 388.46 |
| 335 | 4-Trifluoromethoxyphenyl | t-Butyloxy | 428.41 |
| 336 | 2,4,6-Trimethylphenyl | t-Butyloxy | 386.49 |
| 337 | 4-tert-Butylphenyl | t-Butyloxy | 400.52 |
| 338 | 3,5-Dimethoxyphenyl | t-Butyloxy | 404.46 |
| 339 | —CH₂—C(CH₃)₃ | t-Butyloxy | 338.45 |
| 340 | 4-Ethylphenyl | t-Butyloxy | 372.46 |
| 341 | Thiophen-2-yl | t-Butyloxy | 349.43 |
| 342 | -Phenyl-CO₂—CH₃ | t-Butyloxy | 402.45 |
| 343 | 4-Phenoxyphenyl | t-Butyloxy | 436.51 |

TABLE 3-continued

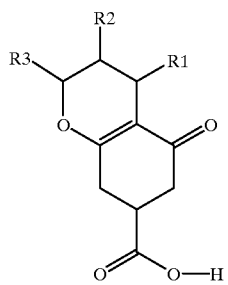

R² = hydrogen

| Ex. | R¹ | R³ | Chem. mass |
|---|---|---|---|
| 344 | —C(CH₃)=CH-phenyl-C(CH₃)₃ | t-Butyloxy | 440.58 |
| 345 | —CH₂—CH(CH₃)-phenyl | t-Butyloxy | 386.49 |
| 346 | —CH(CH₃)—CH(CH₃)—C₂H₅ | t-Butyloxy | 352.47 |
| 347 | 2,5-Dimethyl-4-methoxy-phenyl | t-Butyloxy | 402.49 |
| 348 | 3,5-Dichloro-2-hydroxyphenyl | t-Butyloxy | 429.30 |
| 349 | 3,4-(Methylenedioxy)-6-nitro-phenyl | t-Butyloxy | 433.42 |
| 350 | 3,5-Dimethoxy-2-methyl-phenyl | t-Butyloxy | 418.49 |
| 351 | 3-Ethoxy-4-methoxyphenyl | t-Butyloxy | 418.49 |
| 352 | 3-Ethoxy-4-phenylphenyl | t-Butyloxy | 450.53 |
| 353 | —C₁₂H₂₅ | t-Butyloxy | 436.63 |
| 354 | 2,3-Dimethyl-4-methoxy-phenyl | t-Butyloxy | 402.49 |
| 355 | 3-Hydroxy-4-nitrophenyl | t-Butyloxy | 405.41 |
| 356 | 2-Ethoxy-3,5-dimethoxy-phenyl | t-Butyloxy | 448.52 |
| 357 | 3-Bromo-2,4-dimethoxy-phenyl | t-Butyloxy | 483.36 |
| 358 | 2,4-Dimethoxy-3-phenyl | t-Butyloxy | 418.49 |
| 359 | 4-N—(C₄H₉)-2-phenyl | t-Butyloxy | 471.64 |
| 360 | 3-Bromo-3-methoxyphenyl | t-Butyloxy | 453.33 |
| 361 | 9-Anthracenyl | t-Butyloxy | 444.53 |
| 362 | 2-Hydroxy-3,5-diiodophenyl | t-Butyloxy | 612.20 |
| 363 | 3-Bromo-6-hydroxy-5-methoxyphenyl | t-Butyloxy | 469.33 |
| 364 | —CH₂—CH₂—CH₃ | n-Propyloxy | 296.37 |
| 365 | 4-Quinolyl | n-Propyloxy | 381.43 |
| 366 | —CH₂—CH₂-phenyl | n-Propyloxy | 358.44 |
| 367 | 4-Methoxy-3-methylphenyl | n-Propyloxy | 374.44 |
| 368 | 4-Trifluoromethoxyphenyl | n-Propyloxy | 414.38 |
| 369 | 2,4,6-Trimethylphenyl | n-Propyloxy | 372.46 |
| 370 | 4-tert-Butylphenyl | n-Propyloxy | 386.49 |
| 371 | 3,5-Dimethoxyphenyl | n-Propyloxy | 390.44 |
| 372 | —CH₂—C(CH₃)₃ | n-Propyloxy | 324.42 |
| 373 | 4-Ethylphenyl | n-Propyloxy | 358.44 |
| 374 | Thiophen-2-yl | n-Propyloxy | 335.40 |
| 375 | -Phenyl-CO₂—CH₃ | n-Propyloxy | 388.42 |
| 376 | 4-Phenoxyphenyl | n-Propyloxy | 422.48 |
| 377 | —C(CH₃)=CH-phenyl-C(CH₃)₃ | n-Propyloxy | 426.56 |
| 378 | —CH₂—CH(CH₃)-phenyl | n-Propyloxy | 372.46 |
| 379 | —CH(CH₃)—CH(CH₃)—C₂H₅ | n-Propyloxy | 338.45 |
| 380 | 2,5-Dimethyl-4-methoxy-phenyl | n-Propyloxy | 388.46 |
| 381 | 3,5-Dichloro-2-hydroxyphenyl | n-Propyloxy | 415.27 |
| 382 | 3,4-(Methylenedioxy)-6-nitro-phenyl | n-Propyloxy | 419.39 |
| 383 | 3,5-Dimethoxy-2-methyl-phenyl | n-Propyloxy | 404.46 |
| 384 | 3-Ethoxy-4-methoxyphenyl | n-Propyloxy | 404.46 |
| 385 | 3-Ethoxy-4-phenylphenyl | n-Propyloxy | 436.51 |
| 386 | —C₁₂H₂₅ | n-Propyloxy | 422.61 |
| 387 | 2,3-Dimethyl-4-methoxy-phenyl | n-Propyloxy | 388.46 |
| 388 | 3-Hydroxy-4-nitrophenyl | n-Propyloxy | 391.38 |
| 389 | 2-Ethoxy-3,5-dimethoxy-phenyl | n-Propyloxy | 434.49 |

TABLE 3-continued

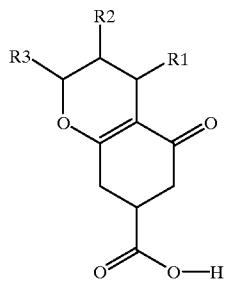

R² = hydrogen

| Ex. | R¹ | R³ | Chem. mass |
|---|---|---|---|
| 390 | 3-Bromo-2,4-dimethoxy-phenyl | n-Propyloxy | 469.33 |
| 391 | 2,4-Dimethoxy-3-phenyl | n-Propyloxy | 404.46 |
| 392 | 4-N—(C₄H₉)₂-phenyl | n-Propyloxy | 457.61 |
| 393 | 3-Bromo-3-methoxyphenyl | n-Propyloxy | 439.31 |
| 394 | 9-Anthracenyl | n-Propyloxy | 430.50 |
| 395 | 2-Hydroxy-3,5-diiodophenyl | n-Propyloxy | 598.18 |
| 396 | 3-Bromo-6-hydroxy-5-methoxyphenyl | n-Propyloxy | 455.30 |
| 397 | —CH₂—CH₂—CH₃ | Methoxy | 268.31 |
| 398 | 4-Quinolyl | Methoxy | 353.38 |
| 399 | —CH₂—CH₂-phenyl | Methoxy | 330.38 |
| 400 | 4-Methoxy-3-methylphenyl | Methoxy | 346.38 |
| 401 | 4-Trifluoromethoxyphenyl | Methoxy | 386.33 |
| 402 | 2,4,6-Trimethylphenyl | Methoxy | 344.41 |
| 403 | 4-tert-Butylphenyl | Methoxy | 358.44 |
| 404 | 3,5-Dimethoxyphenyl | Methoxy | 362.38 |
| 405 | —CH₂—C(CH₃)₃ | Methoxy | 296.37 |
| 406 | 4-Ethylphenyl | Methoxy | 330.38 |
| 407 | Thiophen-2-yl | Methoxy | 307.35 |
| 408 | -Phenyl-CO₂—CH₃ | Methoxy | 360.37 |
| 409 | 4-Phenoxyphenyl | Methoxy | 394.43 |
| 410 | —C(CH₃)=CH-phenyl-C(CH₃)₃ | Methoxy | 398.50 |
| 411 | —CH₂—CH(CH₃)-phenyl | Methoxy | 344.41 |
| 412 | —CH(CH₃)—CH(CH₃)—C₂H₅ | Methoxy | 310.39 |
| 413 | 2,5-Dimethyl-4-methoxy-phenyl | Methoxy | 360.41 |
| 414 | 3,5-Dichloro-2-hydroxyphenyl | Methoxy | 387.22 |
| 415 | 3,4-(Methylenedioxy)-6-nitro-phenyl | Methoxy | 391.34 |
| 416 | 3,5-Dimethoxy-2-methyl-phenyl | Methoxy | 376.41 |
| 417 | 3-Ethoxy-4-methoxyphenyl | Methoxy | 376.41 |
| 418 | 3-Ethoxy-4-phenylphenyl | Methoxy | 408.45 |
| 419 | —C₁₂H₂₅ | Methoxy | 394.55 |
| 420 | 2,3-Dimethyl-4-methoxy-phenyl | Methoxy | 360.41 |
| 421 | 3-Hydroxy-4-nitrophenyl | Methoxy | 363.33 |
| 422 | 2-Ethoxy-3,5-dimethoxy-phenyl | Methoxy | 406.43 |
| 423 | 3-Bromo-2,4-dimethoxy-phenyl | Methoxy | 441.28 |
| 424 | 2,4-Dimethoxy-3-phenyl | Methoxy | 376.41 |
| 425 | 4-N—(C₄H₉)₂-phenyl | Methoxy | 429.56 |
| 426 | 3-Bromo-3-methoxyphenyl | Methoxy | 411.25 |
| 427 | 9-Anthracenyl | Methoxy | 402.45 |
| 428 | 2-Hydroxy-3,5-diiodophenyl | Methoxy | 570.12 |
| 429 | 3-Bromo-6-hydroxy-5-methoxyphenyl | Methoxy | 427.25 |
| 430 | —CH₂—CH₂—CH₃ | —N(CH₃)—CO—CH₃ | 309.36 |
| 431 | 4-Quinolyl | —N(CH₃)—CO—CH₃ | 394.43 |
| 432 | —CH₂—CH₂-phenyl | —N(CH₃)—CO—CH₃ | 371.44 |
| 433 | 4-Methoxy-3-methylphenyl | —N(CH₃)—CO—CH₃ | 387.43 |
| 434 | 4-Trifluoromethoxyphenyl | —N(CH₃)—CO—CH₃ | 427.38 |
| 435 | 2,4,6-Trimethylphenyl | —N(CH₃)—CO—CH₃ | 385.46 |
| 436 | 4-tert-Butylphenyl | —N(CH₃)—CO—CH₃ | 399.49 |
| 437 | 3,5-Dimethoxyphenyl | —N(CH₃)—CO—CH₃ | 403.43 |
| 438 | —CH₂—C(CH₃)₃ | —N(CH₃)—CO—CH₃ | 337.42 |
| 439 | 4-Ethylphenyl | —N(CH₃)—CO—CH₃ | 371.44 |
| 440 | Thiophen-2-yl | —N(CH₃)—CO—CH₃ | 348.40 |

TABLE 3-continued

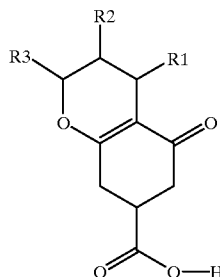

R² = hydrogen

| Ex. | R¹ | R³ | Chem. mass |
|---|---|---|---|
| 441 | —C₆H₄—CO₂—CH₃ | —N(CH₃)—CO—CH₃ | 401.42 |
| 442 | 4-Phenoxyphenyl | —N(CH₃)—CO—CH₃ | 435.48 |
| 443 | —C(CH₃)=CH—C₆H₄—C(CH₃)₃ | —N(CH₃)—CO—CH₃ | 439.55 |
| 444 | —CH₂—CH(CH₃)—C₆H₅ | —N(CH₃)—CO—CH₃ | 385.46 |
| 445 | —CH(CH₃)—CH(CH₃)—C₂H₅ | —N(CH₃)—CO—CH₃ | 351.44 |
| 446 | 2,5-Dimethyl-4-methoxy-phenyl | —N(CH₃)—CO—CH₃ | 401.46 |
| 447 | 3,5-Dichloro-2-hydroxyphenyl | —N(CH₃)—CO—CH₃ | 428.27 |
| 448 | 3,4-(Methylenedioxy)-6-nitro-phenyl | —N(CH₃)—CO—CH₃ | 432.39 |
| 449 | 3,5-Dimethoxy-2-methyl-phenyl | —N(CH₃)—CO—CH₃ | 417.46 |
| 450 | 3-Ethoxy-4-methoxyphenyl | —N(CH₃)—CO—CH₃ | 417.46 |
| 451 | 3-Ethoxy-4-phenylphenyl | —N(CH₃)—CO—CH₃ | 449.51 |
| 452 | —C₁₂H₂₅ | —N(CH₃)—CO—CH₃ | 435.61 |
| 453 | 2,3-Dimethyl-4-methoxy-phenyl | —N(CH₃)—CO—CH₃ | 401.46 |
| 454 | 3-Hydroxy-4-nitrophenyl | —N(CH₃)—CO—CH₃ | 404.38 |
| 455 | 2-Ethoxy-3,5-dimethoxy-phenyl | —N(CH₃)—CO—CH₃ | 447.49 |
| 456 | 3-Bromo-2,4-dimethoxy-phenyl | —N(CH₃)—CO—CH₃ | 482.33 |
| 457 | 2,4-Dimethoxy-3-phenyl | —N(CH₃)—CO—CH₃ | 417.46 |
| 458 | 4-N—(C₄H₉)₂-phenyl | —N(CH₃)—CO—CH₃ | 470.61 |
| 459 | 3-Bromo-3-methoxyphenyl | —N(CH₃)—CO—CH₃ | 452.30 |
| 460 | 9-Anthracenyl | —N(CH₃)—CO—CH₃ | 443.50 |
| 461 | 2-Hydroxy-3,5-diiodophenyl | —N(CH₃)—CO—CH₃ | 611.17 |
| 462 | 3-Bromo-6-hydroxy-5-methoxyphenyl | —N(CH₃)—CO—CH₃ | 468.30 |
| 463 | —CH₂—CH₂—CH₃ | —O—CH₂—CH₂—N—(C₂H₅)₂ | 353.46 |
| 464 | 4-Quinolyl | —O—CH₂—CH₂—N—(C₂H₅)₂ | 438.53 |
| 465 | —CH₂—CH₂-phenyl | —O—CH₂—CH₂—N—(C₂H₅)₂ | 415.53 |
| 466 | 4-Methoxy-3-methylphenyl | —O—CH₂—CH₂—N—(C₂H₅)₂ | 431.53 |
| 467 | 4-Trifluoromethoxyphenyl | —O—CH₂—CH₂—N—(C₂H₅)₂ | 471.48 |
| 468 | 2,4,6-Trimethylphenyl | —O—CH₂—CH₂—N—(C₂H₅)₂ | 429.56 |
| 469 | 4-tert-Butylphenyl | —O—CH₂—CH₂—N—(C₂H₅)₂ | 443.59 |
| 470 | 3,5-Dimethoxyphenyl | —O—CH₂—CH₂—N—(C₂H₅)₂ | 447.53 |
| 471 | —CH₂—C(CH₃)₃ | —O—CH₂—CH₂—N—(C₂H₅)₂ | 381.51 |
| 472 | 4-Ethylphenyl | —O—CH₂—CH₂—N—(C₂H₅)₂ | 415.53 |
| 473 | Thiophen-2-yl | —O—CH₂—CH₂—N—(C₂H₅)₂ | 392.50 |
| 474 | -Phenyl-CO₂—CH₃ | —O—CH₂—CH₂—N—(C₂H₅)₂ | 445.52 |
| 475 | 4-Phenoxyphenyl | —O—CH₂—CH₂—N—(C₂H₅)₂ | 479.58 |
| 476 | —C(CH₃)=CH-phenyl-C(CH₃)₃ | —O—CH₂—CH₂—N—(C₂H₅)₂ | 483.65 |
| 477 | —CH₂—CH(CH₃)-phenyl | —O—CH₂—CH₂—N—(C₂H₅)₂ | 429.56 |
| 478 | —CH(CH₃)—CH(CH₃)—C₂H₅ | —O—CH₂—CH₂—N—(C₂H₅)₂ | 395.54 |
| 479 | 2,5-Dimethyl-4-methoxy-phenyl | —O—CH₂—CH₂—N—(C₂H₅)₂ | 445.56 |
| 480 | 3,5-Dichloro-2-hydroxyphenyl | —O—CH₂—CH₂—N—(C₂H₅)₂ | 472.37 |
| 481 | 3,4-(Methylenedioxy)-6-nitro-phenyl | —O—CH₂—CH₂—N—(C₂H₅)₂ | 476.49 |
| 482 | 3,5-Dimethoxy-2-methyl-phenyl | —O—CH₂—CH₂—N—(C₂H₅)₂ | 461.56 |
| 483 | 3-Ethoxy-4-methoxyphenyl | —O—CH₂—CH₂—N—(C₂H₅)₂ | 461.56 |
| 484 | 3-Ethoxy-4-phenylphenyl | —O—CH₂—CH₂—N—(C₂H₅)₂ | 493.60 |
| 485 | —C₁₂H₂₅ | —O—CH₂—CH₂—N—(C₂H₅)₂ | 479.70 |
| 486 | 2,3-Dimethyl-4-methoxy-phenyl | —O—CH₂—CH₂—N—(C₂H₅)₂ | 445.56 |
| 487 | 3-Hydroxy-4-nitrophenyl | —O—CH₂—CH₂—N—(C₂H₅)₂ | 448.48 |

TABLE 3-continued

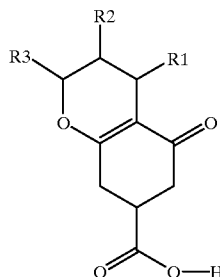

$R^2$ = hydrogen

| Ex. | $R^1$ | $R^3$ | Chem. mass |
|---|---|---|---|
| 488 | 2-Ethoxy-3,5-dimethoxy-phenyl | —O—CH$_2$—CH$_2$—N—(C$_2$H$_5$)$_2$ | 491.58 |
| 489 | 3-Bromo-2,4-dimethoxy-phenyl | —O—CH$_2$—CH$_2$—N—(C$_2$H$_5$)$_2$ | 526.43 |
| 490 | 2,4-Dimethoxy-3-phenyl | —O—CH$_2$—CH$_2$—N—(C$_2$H$_5$)$_2$ | 461.56 |
| 491 | 4-N—(C$_4$H$_9$)$_2$-phenyl | —O—CH$_2$—CH$_2$—N—(C$_2$H$_5$)$_2$ | 514.71 |
| 492 | 3-Bromo-3-methoxyphenyl | —O—CH$_2$—CH$_2$—N—(C$_2$H$_5$)$_2$ | 496.40 |
| 493 | 9-Anthracenyl | —O—CH$_2$—CH$_2$—N—(C$_2$H$_5$)$_2$ | 487.60 |
| 494 | 2-Hydroxy-3,5-diiodophenyl | —O—CH$_2$—CH$_2$—N—(C$_2$H$_5$)$_2$ | 655.27 |
| 495 | 3-Bromo-6-hydroxy-5-methoxyphenyl | —O—CH$_2$—CH$_2$—N—(C$_2$H$_5$)$_2$ | 512.40 |
| 496 | —CH$_2$—CH$_2$—CH$_3$ | —O—CH$_2$-cyclohexyl-CH$_2$—OH | 380.48 |
| 497 | 4-Quinolyl | —O—CH$_2$-cyclohexyl-CH$_2$—OH | 465.55 |
| 498 | —CH$_2$—CH$_2$-phenyl | —O—CH$_2$-cyclohexyl-CH$_2$—OH | 442.55 |
| 499 | 4-Methoxy-3-methylphenyl | —O—CH$_2$-cyclohexyl-CH$_2$—OH | 458.55 |
| 500 | 4-Trifluoromethoxyphenyl | —O—CH$_2$-cyclohexyl-CH$_2$—OH | 498.50 |
| 501 | 2,4,6-Trimethylphenyl | —O—CH$_2$-cyclohexyl-CH$_2$—OH | 456.58 |
| 502 | 4-tert-Butylphenyl | —O—CH$_2$-cyclohexyl-CH$_2$—OH | 470.61 |
| 503 | 3,5-Dimethoxyphenyl | —O—CH$_2$-cyclohexyl-CH$_2$—OH | 474.55 |
| 504 | —CH$_2$—C(CH$_3$)$_3$ | —O—CH$_2$-cyclohexyl-CH$_2$—OH | 408.54 |
| 505 | 4-Ethylphenyl | —O—CH$_2$-cyclohexyl-CH$_2$—OH | 442.55 |
| 506 | Thiophen-2-yl | —O—CH$_2$-cyclohexyl-CH$_2$—OH | 419.52 |
| 507 | -Phenyl-CO$_2$—CH$_3$ | —O—CH$_2$-cyclohexyl-CH$_2$—OH | 472.54 |
| 508 | 4-Phenoxyphenyl | —O—CH$_2$-cyclohexyl-CH$_2$—OH | 506.60 |
| 509 | —C(CH$_3$)=CH-phenyl-C(CH$_3$)$_3$ | —O—CH$_2$-cyclohexyl-CH$_2$—OH | 510.67 |
| 510 | —CH$_2$—CH(CH$_3$)-phenyl | —O—CH$_2$-cyclohexyl-CH$_2$—OH | 456.58 |
| 511 | —CH(CH$_3$)—CH(CH$_3$)—C$_2$H$_5$ | —O—CH$_2$-cyclohexyl-CH$_2$—OH | 422.56 |
| 512 | 2,5-Dimethyl-4-methoxy-phenyl | —O—CH$_2$-cyclohexyl-CH$_2$—OH | 472.58 |
| 513 | 3,5-Dichloro-2-hydroxyphenyl | —O—CH$_2$-cyclohexyl-CH$_2$—OH | 499.39 |
| 514 | 3,4-(Methylenedioxy)-6-nitro-phenyl | —O—CH$_2$-cyclohexyl-CH$_2$—OH | 503.51 |
| 515 | 3,5-Dimethoxy-2-methyl-phenyl | —O—CH$_2$-cyclohexyl-CH$_2$—OH | 488.58 |
| 516 | 3-Ethoxy-4-methoxyphenyl | —O—CH$_2$-cyclohexyl-CH$_2$—OH | 488.58 |
| 517 | 3-Ethoxy-4-phenylphenyl | —O—CH$_2$-cyclohexyl-CH$_2$—OH | 520.63 |
| 518 | —C$_{12}$H$_{25}$ | —O—CH$_2$-cyclohexyl-CH$_2$—OH | 506.73 |
| 519 | 2,3-Dimethyl-4-methoxy-phenyl | —O—CH$_2$-cyclohexyl-CH$_2$—OH | 472.58 |
| 520 | 3-Hydroxy-4-nitrophenyl | —O—CH$_2$-cyclohexyl-CH$_2$—OH | 475.50 |
| 521 | 2-Ethoxy-3,5-dimethoxy-phenyl | —O—CH$_2$-cyclohexyl-CH$_2$—OH | 518.61 |
| 522 | 3-Bromo-2,4-dimethoxy-phenyl | —O—CH$_2$-cyclohexyl-CH$_2$—OH | 553.45 |
| 523 | 2,4-Dimethoxy-3-phenyl | —O—CH$_2$-cyclohexyl-CH$_2$—OH | 488.58 |
| 524 | 4-N—(C$_4$H$_9$)$_2$-phenyl | —O—CH$_2$-cyclohexyl-CH$_2$—OH | 541.73 |
| 525 | 3-Bromo-3-methoxyphenyl | —O—CH$_2$-cyclohexyl-CH$_2$—OH | 523.42 |
| 526 | 9-Anthracenyl | —O—CH$_2$-cyclohexyl-CH$_2$—OH | 514.62 |
| 527 | 2-Hydroxy-3,5-diiodophenyl | —O—CH$_2$-cyclohexyl-CH$_2$—OH | 682.29 |
| 528 | 3-Bromo-6-hydroxy-5-methoxyphenyl | —O—CH$_2$-cyclohexyl-CH$_2$—OH | 539.42 |
| 529 | —CH$_2$—CH$_2$—CH$_3$ | —O—C(CH$_3$)$_2$—CH$_2$—CH$_3$ | 324.42 |
| 530 | 4-Quinolyl | —O—C(CH$_3$)$_2$—CH$_2$—CH$_3$ | 409.48 |
| 531 | —CH$_2$—CH$_2$-phenyl | —O—C(CH$_3$)$_2$—CH$_2$—CH$_3$ | 386.49 |
| 532 | 4-Methoxy-3-methylphenyl | —O—C(CH$_3$)$_2$—CH$_2$—CH$_3$ | 402.49 |
| 533 | 4-Trifluoromethoxyphenyl | —O—C(CH$_3$)$_2$—CH$_2$—CH$_3$ | 442.43 |
| 534 | 2,4,6-Trimethylphenyl | —O—C(CH$_3$)$_2$—CH$_2$—CH$_3$ | 400.52 |
| 535 | 4-tert-Butylphenyl | —O—C(CH$_3$)$_2$—CH$_2$—CH$_3$ | 414.54 |
| 536 | 3,5-Dimethoxyphenyl | —O—C(CH$_3$)$_2$—CH$_2$—CH$_3$ | 418.49 |
| 537 | —CH$_2$—C(CH$_3$)$_3$ | —O—C(CH$_3$)$_2$—CH$_2$—CH$_3$ | 352.47 |

TABLE 3-continued

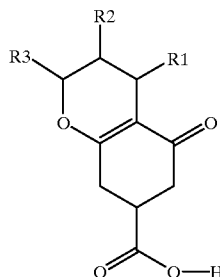

R² = hydrogen

| Ex. | R¹ | R³ | Chem. mass |
|---|---|---|---|
| 538 | 4-Ethylphenyl | —O—C(CH₃)₂—CH₂—CH₃ | 386.49 |
| 539 | Thiophen-2-yl | —O—C(CH₃)₂—CH₂—CH₃ | 363.46 |
| 540 | -Phenyl-CO₂—CH₃ | —O—C(CH₃)₂—CH₂—CH₃ | 416.47 |
| 541 | 4-Phenoxyphenyl | —O—C(CH₃)₂—CH₂—CH₃ | 450.53 |
| 542 | —C(CH₃)=CH-phenyl-C(CH₃)₃ | —O—C(CH₃)₂—CH₂—CH₃ | 454.61 |
| 543 | —CH₂—CH(CH₃)-phenyl | —O—C(CH₃)₂—CH₂—CH₃ | 400.52 |
| 544 | —CH(CH₃)—CH(CH₃)—C₂H₅ | —O—C(CH₃)₂—CH₂—CH₃ | 366.50 |
| 545 | 2,5-Dimethyl-4-methoxy-phenyl | —O—C(CH₃)₂—CH₂—CH₃ | 416.52 |
| 546 | 3,5-Dichloro-2-hydroxyphenyl | —O—C(CH₃)₂—CH₂—CH₃ | 443.33 |
| 547 | 3,4-(Methylenedioxy)-6-nitro-phenyl | —O—C(CH₃)₂—CH₂—CH₃ | 447.44 |
| 548 | 3,5-Dimethoxy-2-methyl-phenyl | —O—C(CH₃)₂—CH₂—CH₃ | 432.52 |
| 549 | 3-Ethoxy-4-methoxyphenyl | —O—C(CH₃)₂—CH₂—CH₃ | 432.52 |
| 550 | 3-Ethoxy-4-phenylphenyl | —O—C(CH₃)₂—CH₂—CH₃ | 464.56 |
| 551 | —C₁₂H₂₅ | —O—C(CH₃)₂—CH₂—CH₃ | 450.66 |
| 552 | 2,3-Dimethyl-4-methoxy-phenyl | —O—C(CH₃)₂—CH₂—CH₃ | 416.52 |
| 553 | 3-Hydroxy-4-nitrophenyl | —O—C(CH₃)₂—CH₂—CH₃ | 419.43 |
| 554 | 2-Ethoxy-3,5-dimethoxy-phenyl | —O—C(CH₃)₂—CH₂—CH₃ | 462.54 |
| 555 | 3-Bromo-2,4-dimethoxy-phenyl | —O—C(CH₃)₂—CH₂—CH₃ | 497.39 |
| 556 | 2,4-Dimethoxy-3-phenyl | —O—C(CH₃)₂—CH₂—CH₃ | 432.52 |
| 557 | 4-N—(C₄H₉)₂-phenyl | —O—C(CH₃)₂—CH₂—CH₃ | 485.67 |
| 558 | 3-Bromo-3-methoxyphenyl | —O—C(CH₃)₂—CH₂—CH₃ | 467.36 |
| 559 | 9-Anthracenyl | —O—C(CH₃)₂—CH₂—CH₃ | 458.56 |
| 560 | 2-Hydroxy-3,5-diiodophenyl | —O—C(CH₃)₂—CH₂—CH₃ | 626.23 |
| 561 | 3-Bromo-6-hydroxy-5-methoxyphenyl | —O—C(CH₃)₂—CH₂—CH₃ | 483.36 |

TABLE 4

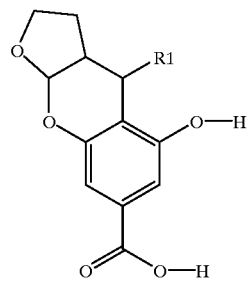

| Ex. | R¹ | Chem. mass |
|---|---|---|
| 1 | —CH₃—CH₂—CH₃ | 278.31 |
| 2 | 4-Quinolyl | 363.37 |
| 3 | —CH₂—CH₂—phenyl | 340.38 |
| 4 | 4-Methoxy-3-methylphenyl | 356.38 |
| 5 | 4-Trifluoromethoxyphenyl | 396.32 |

TABLE 4-continued

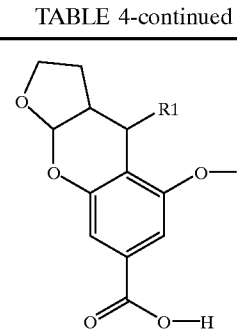

| Ex. | R¹ | Chem. mass |
|---|---|---|
| 6 | 2,4,6-Trimethylphenyl | 354.40 |
| 7 | 4-tert-Butylphenyl | 368.43 |
| 8 | 3,5-Dimethoxyphenyl | 372.38 |
| 9 | —CH₂—C(CH₃)₃ | 306.36 |
| 10 | 4-Ethylphenyl | 340.38 |

TABLE 4-continued

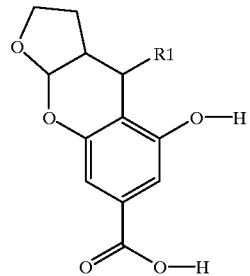

| Ex. | R¹ | Chem. mass |
|---|---|---|
| 11 | Thiophen-2-yl | 317.34 |
| 12 | —Phenyl—CO₂—CH₃ | 370.36 |
| 13 | 4-Phenoxyphenyl | 404.42 |
| 14 | —C(CH₃)=CH—phenyl—C(CH₃)₃ | 408.50 |
| 15 | —CH₂—CH(CH₃)—phenyl | 354.40 |
| 16 | —CH(CH₃)—CH(CH₃)—C₂H₅ | 320.39 |
| 17 | 2,5-Dimethyl-4-methoxyphenyl | 370.40 |
| 18 | 3,5-Diohloro-2-hydroxyphenyl | 397.21 |
| 19 | 3,4-(Methylenedioxy)-6-nitrophenyl | 401.33 |
| 20 | 3,5-Dimethoxy-2-methylphenyl | 386.40 |
| 21 | 3-Ethoxy-4-methoxyphenyl | 386.40 |
| 22 | 3-Ethoxy-4-phenylphenyl | 418.45 |
| 23 | —C₁₂H₂₅ | 404.55 |
| 24 | 2,3-Dimethyl-4-methoxyphenyl | 370.40 |
| 25 | 3-Hydroxy-4-nitrophenyl | 373.32 |
| 26 | 2-Ethoxy-3,5-dimethoxyphenyl | 416.43 |
| 27 | 3-Bromo-2,4-dimethoxyphenyl | 451.27 |
| 28 | 2,4-Dimethoxy-3-phenyl | 386.40 |
| 29 | 4-N-(C₄H₉)₂—phenyl | 439.55 |
| 30 | 3-Bromo-3-methoxyphenyl | 421.25 |
| 31 | 9-Anthracenyl | 412.44 |
| 32 | 2-Hydroxy-3,5-diiodophenyl | 580.12 |
| 33 | 3-Bromo-6-hydroxy-5-methoxyphenyl | 437.25 |

TABLE 5

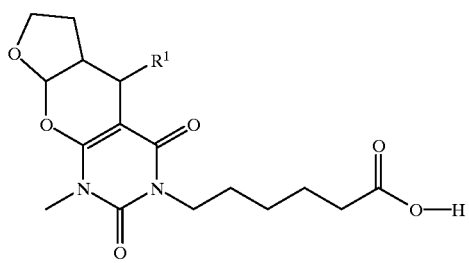

| Ex. | R¹ | Chem. mass |
|---|---|---|
| 1 | —CH₂—CH₂—CH₃ | 380.44 |
| 2 | 4-Quinolyl | 465.51 |
| 3 | —CH₂—CH₂—phenyl | 442.51 |
| 4 | 4-Methoxy-3-methylphenyl | 458.51 |
| 5 | 4-Trifluoromethoxyphenyl | 498.46 |
| 6 | 2,4,6-Trimethylphenyl | 456.54 |
| 7 | 4-tert-Butylphenyl | 470.57 |
| 8 | 3,5-Dimethoxyphenyl | 474.51 |
| 9 | —CH₂—C(CH₃)₃ | 408.50 |
| 10 | 4-Ethylphenyl | 442.51 |
| 11 | Thiophen-2-yl | 419.48 |
| 12 | —Phenyl—CO₂—CH₃ | 472.50 |
| 13 | 4-Phenoxyphenyl | 506.56 |
| 14 | —C(CH₃)=CH—phenyl—C(CH₃)₃ | 510.63 |
| 15 | —CH₂—CH(CH₃)—phenyl | 456.54 |
| 16 | —CH(CH₃)—CH(CH₃)—C₂H₅ | 422.52 |
| 17 | 2,5-Dimethyl-4-methoxyphenyl | 472.54 |
| 18 | 3,5-Dichloro-2-hydroxyphenyl | 499.35 |
| 19 | 3,4-(Methylenedioxy)-6-nitrophenyl | 503.47 |

TABLE 5-continued

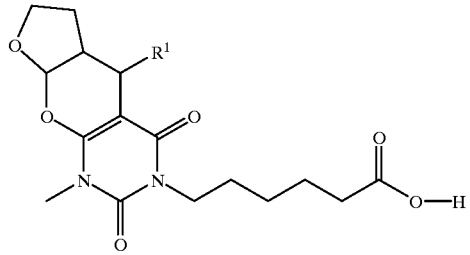

| Ex. | R¹ | Chem. mass |
|---|---|---|
| 20 | 3,5-Dimethoxy-2-methylphenyl | 488.54 |
| 21 | 3-Ethoxy-4-methoxyphenyl | 488.54 |
| 22 | 3-Ethoxy-4-phenylphenyl | 520.59 |
| 23 | —C₁₂H₂₅ | 506.69 |
| 24 | 2,3-Dimethyl-4-methoxyphenyl | 472.54 |
| 25 | 3-Hydroxy-4-nitrophenyl | 475.46 |
| 26 | 2-Ethoxy-3,5-dimethoxyphenyl | 518.57 |
| 27 | 3-Bromo-2,4-dimethoxyphenyl | 553.41 |
| 28 | 2,4-Dimethoxy-3-phenyl | 488.54 |
| 29 | 4-N-(C₄H₉)₂—phenyl | 541.69 |
| 30 | 3-Bromo-3-methoxyphenyl | 523.38 |
| 31 | 9-Anthracenyl | 514.55 |
| 32 | 2-Hydroxy-3,5-diiodophenyl | 682.25 |
| 33 | 3-Bromo-6-hydroxy-5-methoxyphenyl | 539.38 |

What is claimed is:
1. A compound of the formula I

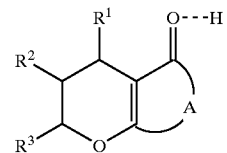

in which:
  R¹ is
  1. $(C_1-C_{14})$-alkyl,
  2. $(C_2-C_6)$-alkenyl,
  3. $(C_0-C_6)$-alkyl-$(C_3-C_{10})$-cycloalkyl-$(C_0-C_6)$-alkyl, where the alkyl moiety is unsubstituted or substituted by one or more OH groups,
  4. $(C_0-C_6)$-alkyl-$(C_6-C_{14})$-aryl,
  5. $(C_0-C_6)$-alkyl-$(C_3-C_9)$-heteroaryl,
  6. $(C_2-C_6)$-alkenyl-$(C_6-C_{14})$-aryl,
  7. $(C_2-C_6)$-alkenyl-$(C_3-C_9)$-heteroaryl,
  8. $(C_1-C_6)$-alkanoyl, or
  9. a radical as defined under 4., 5., 6. or 7., where the $(C_6-C_{14})$-aryl or $(C_3-C_9)$-heteroaryl moiety is substituted by 1, 2 or 3 identical or different radicals selected from the group consisting of $(C_1-C_{10})$-alkyl, carboxyl, amino, nitro, $(C_1-C_4)$-alkylamino, hydroxyl, $(C_1-C_4)$-alkoxy, where one to all hydrogen atoms can be replaced by fluorine atoms, $(C_6-C_{12})$-aryloxy, halogen, cyano, di-$(C_1-C_4)$-alkylamino, carbamoyl, sulfamoyl and $(C_1-C_4)$-alkoxycarbonyl, or two adjacent radicals on the $(C_6-C_{12})$-aryl ring together are alkylenedioxy;

R² is hydrogen, $(C_1-C_{10})$-alkyl, $(C_0-C_6)$-alkyl-$(C_{6-12})$-aryl or $(C_0-C_6)$-alkyl-$(C_3-C_9)$-heteroaryl, where the $C_6-C_{12}$-aryl or $C_3-C_9$-heteroaryl moiety is unsubstituted or substituted by 1, 2 or 3 identical or different radicals selected from the group consisting of carboxyl, amino, $(C_1-C_4)$-alkylamino, hydroxyl, $(C_1-C_4)$- alkoxy, halogen, cyano, di-($C_1$–$C_4$)-alkylamino, carbamoyl, sulfamoyl and ($C_1$–$C_4$)-alkoxycarbonyl;

$R^3$ is —X—$R^4$;

X is —O—, —$NR^5$— or —S—;

$R^4$ is defined as $R^1$;

or, alternatively to the definitions of $R^4$ and $R^2$ above, $R^4$ together with $R^2$ forms a bridge member —$CH_2$—$CH_2$— or —$CH_2$—$CH_2$—$CH_2$—;

$R^5$ is hydrogen or ($C_1$–$C_6$)-alkyl;

A is a fused cyclic ring system which a) is substituted by one, two or three oxo or hydroxyl functions, where one hydroxyl or oxo function is in the neighboring position to the dihydropyran ring, and b) is mono-, di- or polysubstituted by a ($C_1$–$C_{10}$)-alkyl radical or a carboxyl group, where at least one alkyl substituent carries a functional group;

or a physiologically tolerable salt thereof.

2. A compound as claimed in claim 1, wherein $R^1$ is as defined under 9, and the two adjacent radicals on the ($C_6$–$C_{12}$)-aryl ring together are methylenedioxy.

3. A compound as claimed in claim 1, wherein A is a fused cyclic ring system which is substituted by one or two oxo or hydroxyl functions.

4. A compound as claimed in claim 1, wherein A is a fused cyclic ring system which is mono- or disubstituted by a ($C_1$–$C_{10}$)-alkyl radical or a carboxyl group.

5. A compound as claimed in claim 1, wherein A is a fused cyclic ring system that is mono- or di- or polysubstituted by a ($C_1$–$C_{10}$)-alkyl radical or a carboxyl group, where at least one alkyl substituent carries a hydroxyl, carboxyl, or amino group.

6. A compound as claimed in claim 1, wherein A is a fused cyclic ring system which is mono-, di- or polysubstituted by a ($C_1$–$C_{10}$)-alkyl radical or a carboxyl group, where at least one alkyl substituent carries a hydroxyl, carboxyl or amino group.

7. A pharmaceutical composition comprising an effective amount of a compound as claimed in claim 1, together with a pharmaceutically suitable auxiliary.

8. A method for the treatment of a metabolic disorder comprising administering to a host in need of such treatment an effective amount of a compound as claimed in claim 1.

9. A method as claimed in claim 7, wherein the metabolic disorder is diabetes or arteriosclerosis.

10. A method for the treatment of a disorder of the cardiovascular system comprising administering to a host in need of such treatment an effective amount of a compound as claimed in claim 1.

11. A method for the treatment of a disorder of the central nervous system comprising administering to a host in need of such treatment an effective amount of a compound as claimed in claim 1.

12. A method for the treatment of a disorder of bone metabolism comprising administering to a host in need of such treatment an effective amount of a compound as claimed in claim 1.

13. A method for the treatment of cancer comprising administering to a host in need of such treatment an effective amount of a compound as claimed in claim 1.

14. A method for the treatment of an autoimmune disorder comprising administering to a host in need of such treatment an effective amount of a compound as claimed in claim 1.

15. A method for the treatment of infection comprising administering to a host in need of such treatment an effective amount of a compound as claimed in claim 1.

16. A compound as claimed in claim 1, in which the fused cyclic ring system A is 1,3-pyrimidine, benzene, dioxane or cyclohexane.

17. A compound as claimed in claim 1, in which the compound is a compound of formula

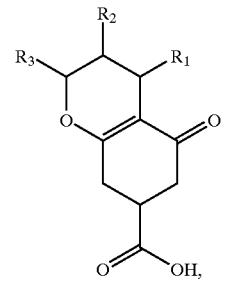

or a physiologically tolerable salt thereof.

18. A compound as claimed in claim 1, in which the compound is a compound of the formula

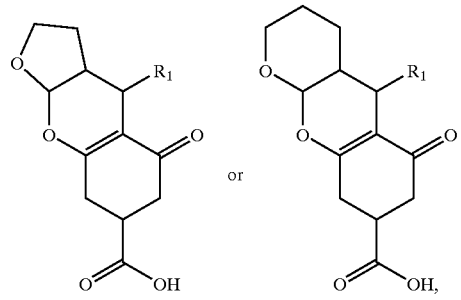

or a physiologically tolerable salt thereof.

* * * * *

UNITED STATES PATENT AND TRADEMARK OFFICE
CERTIFICATE OF CORRECTION

PATENT NO. : 6,399,653 B1
DATED : June 4, 2002
INVENTOR(S) : Henke

It is certified that error appears in the above-identified patent and that said Letters Patent is hereby corrected as shown below:

Title page,
Item [54], in the title, "DIHYDROPYRANS" should read -- DIHYDROPYRANES --.

Column 38,
Line 62, "$(C_{6-12})$" should read -- $(C_6-C_{12})$ --.

Column 39,
Lines 29-33, delete the claim in its entirety.
Line 45, "claim 7" should read -- claim 8 --.

Signed and Sealed this

Twenty-second Day of October, 2002

Attest:

JAMES E. ROGAN
Attesting Officer
Director of the United States Patent and Trademark Office